(12) United States Patent
Sugita et al.

(10) Patent No.: US 9,841,395 B2
(45) Date of Patent: Dec. 12, 2017

(54) SYSTEM OF INSPECTING FOCUS RING AND METHOD OF INSPECTING FOCUS RING

(71) Applicant: TOKYO ELECTRON LIMITED, Tokyo (JP)

(72) Inventors: Kippei Sugita, Miyagi (JP); Tomohide Minami, Miyagi (JP)

(73) Assignee: TOKYO ELECTRON LIMITED, Tokyo (JP)

( * ) Notice: Subject to any disclaimer, the term of this patent is extended or adjusted under 35 U.S.C. 154(b) by 53 days.

(21) Appl. No.: 15/179,306

(22) Filed: Jun. 10, 2016

(65) Prior Publication Data

US 2016/0363556 A1 Dec. 15, 2016

(30) Foreign Application Priority Data

Jun. 11, 2015 (JP) ................. 2015-118183

(51) Int. Cl.
*G01N 27/24* (2006.01)
*G01R 27/26* (2006.01)
(Continued)

(52) U.S. Cl.
CPC ......... *G01N 27/24* (2013.01); *G01R 27/2605* (2013.01); *G01R 31/2831* (2013.01);
(Continued)

(58) Field of Classification Search
CPC ........ G01N 27/00; G01N 27/02; G01N 27/22; G01N 27/24; G01R 27/00; G01R 27/02; G01R 27/26; G01R 27/2605; G01R 31/26; G01R 31/2642; G01R 31/2648; G01R 31/265; G01R 31/2831; G01R 31/318511; G01R 1/0491; G01R 19/00; G06F 3/044; B23K 10/00; B23K 10/02; B23K 37/0461;
(Continued)

(56) References Cited

U.S. PATENT DOCUMENTS 5,314,603 A * 5/1994 Sugiyama ......... H01J 37/32082
156/345.28
8,004,293 B2 * 8/2011 White ................. C23C 16/4585
324/522

(Continued)

FOREIGN PATENT DOCUMENTS

JP 2012-049166 A 3/2012

*Primary Examiner* — Hoai-An D Nguyen
(74) *Attorney, Agent, or Firm* — Pearne & Gordon LLP

(57) ABSTRACT

A system of inspecting a focus ring is provided. The system includes a measuring device, a transfer device and an operation unit. The measuring device includes a base substrate, a sensor chip and a circuit board. The sensor chip has a sensor electrode and is provided along an edge of the base substrate. The circuit board is configured to output a high frequency signal to the sensor electrode and acquire a digital value indicating electrostatic capacitance based on a voltage amplitude in the sensor electrode. The transfer device is configured to scan the measuring device. The operation unit is configured to obtain difference values by performing a difference operation with respect to the digital values acquired by the measuring device at multiple positions along a direction which intersects with an inner periphery of the focus ring.

11 Claims, 17 Drawing Sheets

(51) Int. Cl.
*G01R 31/28* (2006.01)
*H01J 37/32* (2006.01)
*G01R 31/3185* (2006.01)
*G01R 31/265* (2006.01)

(52) U.S. Cl.
CPC ...... *H01J 37/32009* (2013.01); *G01R 31/265* (2013.01); *G01R 31/318511* (2013.01); *H01J 37/321* (2013.01); *H01J 37/32211* (2013.01)

(58) Field of Classification Search
CPC .............. H01J 37/32009; H01J 37/321; H01J 37/32211; H01J 37/32917; H01L 22/00
USPC ....... 324/600, 649, 658, 671, 713, 686, 679, 324/676, 522, 537, 555, 757.01, 757.03, 324/762.01–762.06, 76.11; 156/345.1, 156/345.35; 216/58, 59, 61, 63, 67; 219/121.11, 121.36, 121.39, 121.4, 219/121.43; 315/111.01, 111.21, 111.71, 315/111.81, 111.91
See application file for complete search history.

(56) References Cited

U.S. PATENT DOCUMENTS

| | | | |
|---|---|---|---|
| 2005/0189068 A1* | 9/2005 | Suzuki | H01J 37/32642 156/345.3 |
| 2008/0237182 A1* | 10/2008 | Yamawaku | H01J 37/3244 216/59 |
| 2009/0130783 A1* | 5/2009 | Miyashita | H04R 19/005 438/10 |
| 2010/0243606 A1* | 9/2010 | Koshimizu | H01J 37/32091 216/67 |
| 2012/0160808 A1* | 6/2012 | Kikuchi | H01J 37/32165 216/67 |
| 2014/0231389 A1* | 8/2014 | Nagami | H01J 37/32091 216/67 |

* cited by examiner

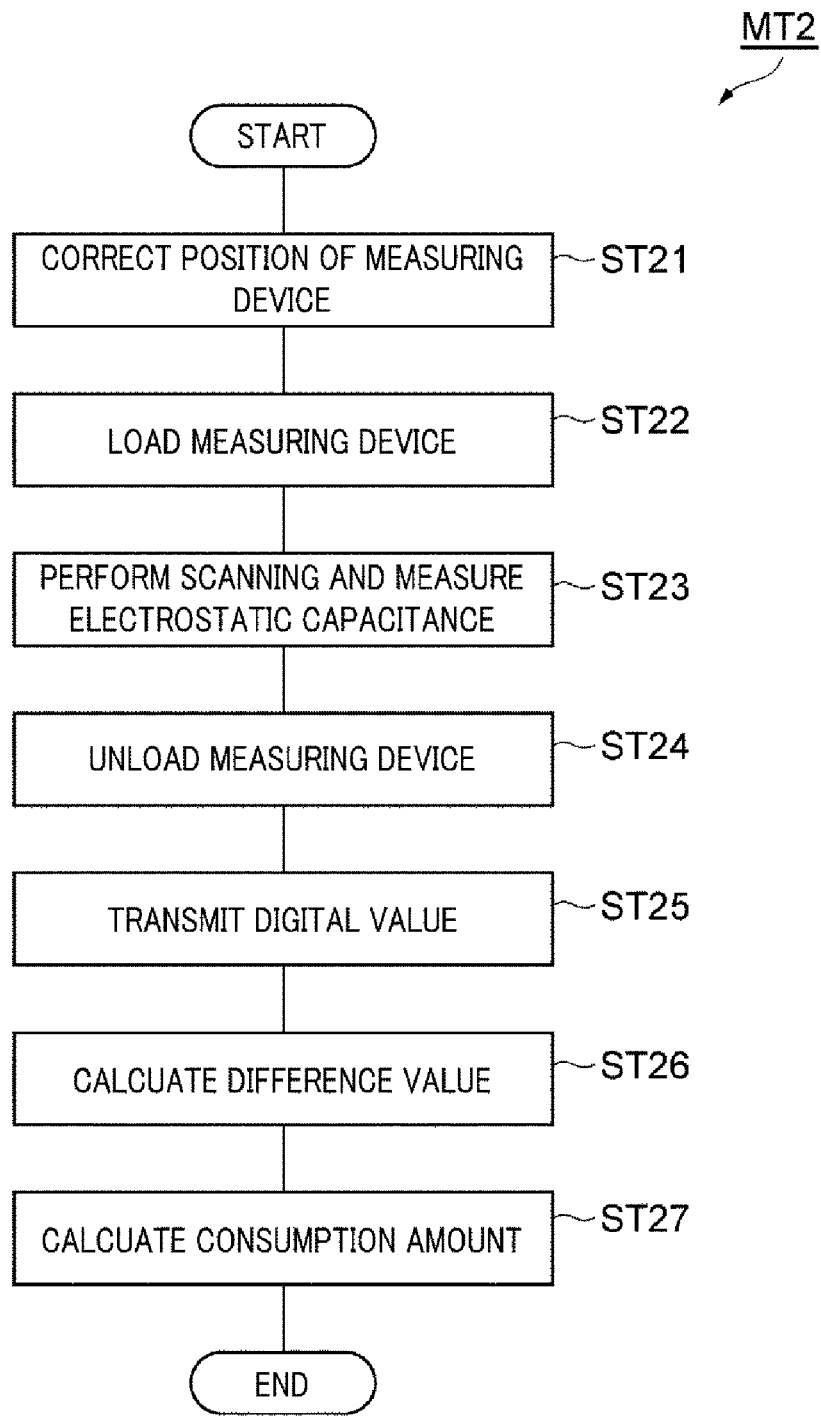

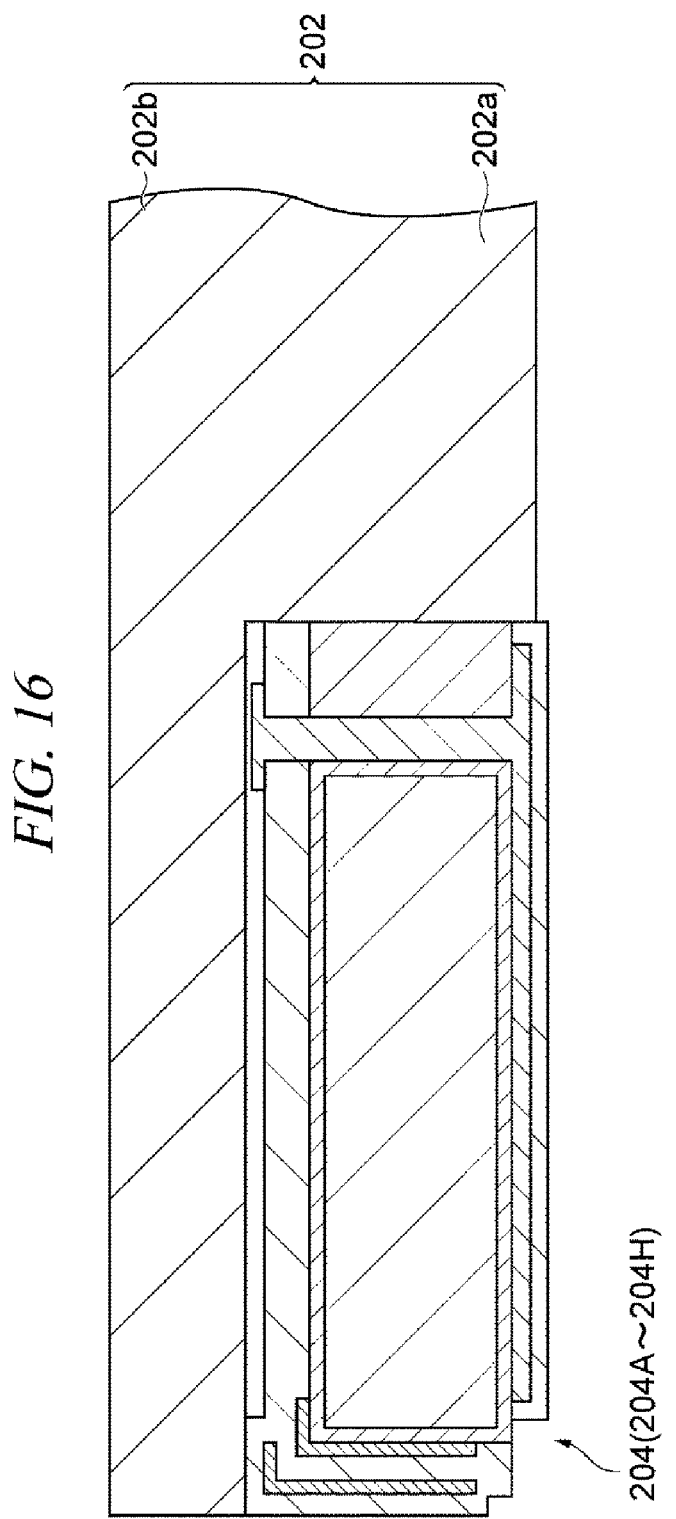

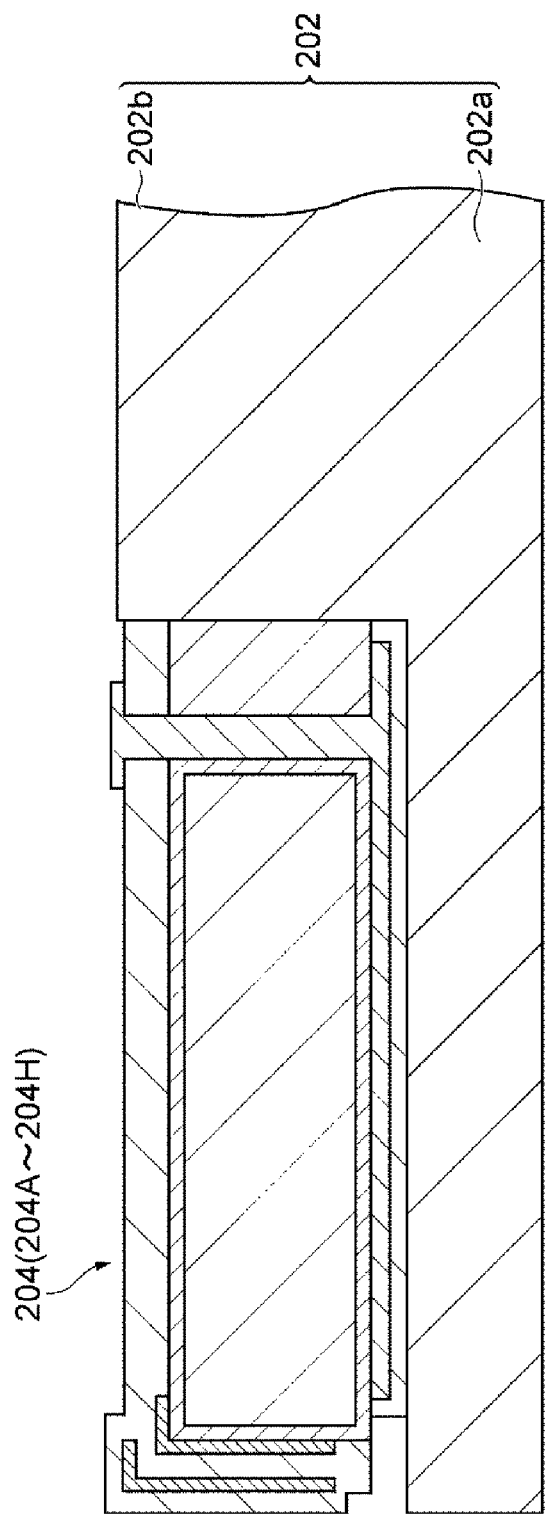

US 9,841,395 B2

SYSTEM OF INSPECTING FOCUS RING AND METHOD OF INSPECTING FOCUS RING

CROSS-REFERENCE TO RELATED APPLICATION

This application claims the benefit of Japanese Patent Application No. 2015-118183 filed on Jun. 11, 2015, the entire disclosures of which are incorporated herein by reference.

TECHNICAL FIELD

The embodiments described herein pertain generally to a system of inspecting a focus ring and a method of inspecting the focus ring.

BACKGROUND

In the manufacture of an electronic device such as a semiconductor device, a plasma processing apparatus is used. Generally, the plasma processing apparatus includes a processing vessel and a mounting table. The mounting table holds a processing target object mounted thereon and is provided within the processing vessel. In the plasma processing apparatus, the processing target object is mounted on the mounting table and is processed by plasma of a processing gas, which is generated within the processing vessel.

In the aforementioned plasma processing apparatus, in order to improve processing uniformity over an entire surface of the processing target object, a focus ring may be provided on the mounting table to surround an edge of the processing target object. The plasma processing apparatus with the focus ring is described in Patent Document 1.

Patent Document 1: Japanese Patent Laid-open Publication No. 2012-049166

In the plasma processing apparatus, the focus ring as well as the processing target object is exposed to active species of molecules or atoms in the processing gas. Accordingly, the focus ring is consumed (worn) by performing a process on the processing target object. If an excessively consumed focus ring is used, the process on the processing target object is adversely affected. Thus, the excessively consumed focus ring needs to be replaced.

From this background, it is required to inspect the focus ring to figure out a consumption amount thereof.

SUMMARY

In one exemplary embodiment, a system of inspecting a focus ring is provided. The focus ring is provided on a mounting table configured to mount thereon a processing target object within a processing vessel of a plasma processing apparatus, and the focus ring has an annular plate-shaped first portion and an annular plate-shaped second portion which is extended on the first portion, and a diameter of an inner periphery of the second portion is larger than a diameter of an inner periphery of the first portion. The system includes a measuring device configured to measure electrostatic capacitance, a transfer device and an operation unit. The measuring device includes a base substrate having a disk shape, a sensor chip and a circuit board. The sensor chip has a sensor electrode and is provided along an edge of the base substrate. The circuit board is configured to output a high frequency signal to the sensor electrode and acquire a digital value indicating electrostatic capacitance based on a voltage amplitude in the sensor electrode. The transfer device is configured to move the sensor chip on the first portion of the focus ring and within a region surrounded by the inner periphery of the second portion of the focus ring by scanning the measuring device. The operation unit is configured to receive the digital values acquired by the measuring device at multiple positions along a direction which intersects with the inner periphery of the second portion of the focus ring, and is configured to obtain difference values at the multiple positions by performing a difference operation with respect to the digital values.

The electrostatic capacitance obtained from the voltage amplitude of the sensor electrode increases as the sensor electrode approaches the inner periphery of the second portion of the focus ring. Further, the degree of this increment decreases if the top face of the first portion of the focus ring is consumed. Accordingly, the multiple difference values at the multiple positions, which are obtained by performing the difference operation with respect to the multiple digital values, reflect the consumption amounts of the first portion at the multiple positions. Thus, according to the system, it is possible to figure out the consumption amount of the first portion of the focus ring.

Further, the operation unit may be configured to calculate a difference between each of the difference values and a preset value corresponding thereto. The difference obtained in the operation unit reflects the consumption amount of the first portion at each position.

The circuit board may include a communication device configured to wirelessly transmit the digital value to the operation unit.

In another exemplary embodiment, a system of inspecting a focus ring is provided. The focus ring is provided on a mounting table configured to mount thereon a processing target object within a processing vessel of a plasma processing apparatus, and the focus ring has an annular plate-shaped first portion and an annular plate-shaped second portion which is extended on the first portion, and a diameter of an inner periphery of the second portion is larger than a diameter of an inner periphery of the first portion. The system includes a measuring device configured to measure electrostatic capacitance, a transfer device and an operation unit. The measuring device includes a base substrate having a disk shape, a sensor chip and a circuit board. The sensor chip has a first sensor electrode and a second sensor electrode. The first sensor electrode faces downwards and the second sensor electrode faces an outside of an edge of the base substrate. The sensor chip is provided along the edge of the base substrate. The circuit board is configured to output a high frequency signal to the first sensor electrode and the second sensor electrode, and acquire a first digital value indicating electrostatic capacitance based on a voltage amplitude in the first sensor electrode and a second digital value indicating electrostatic capacitance based on a voltage amplitude in the second sensor electrode. The transfer device is configured to move the sensor chip on the first portion and within a region surrounded by the inner periphery of the second portion by scanning the measuring device. The operation unit is configured to receive the first digital values and the second digital values acquired by the measuring device at multiple positions along a direction which intersects with the inner periphery of the second portion of the focus ring, and is configured to obtain difference values at the multiple positions by performing a difference operation with respect to the first digital values.

The first digital values are obtained based on the voltage amplitudes in the first sensor electrode which faces downwards, that is, faces the top face of the first portion of the focus ring. Accordingly, the multiple difference values obtained based on the first digital values reflect the consumption amounts of the first portion at the multiple positions. Further, the second digital values are obtained based on the voltage amplitudes in the second sensor electrode which faces the outside of the base substrate, that is, faces the inner periphery of the second portion of the focus ring. Accordingly, the second digital values reflect the consumption amounts of the inner periphery of the second portion. Thus, according to the system, the consumption amounts of the first portion and the second portion of the focus ring can be figured out.

Further, the sensor chip may further include a guard electrode. The guard electrode is provided between the first sensor electrode and the second sensor electrode, and the high frequency signal is sent to the guard electrode. In this exemplary embodiment, due to the shield effect by the guard electrode, the directivity of the first sensor electrode in a downward direction and the directivity of the second sensor electrode toward a direction in which the second portion of the focus ring is located can be improved.

Furthermore, the operation unit may be configured to calculate a difference between each of the difference values and a preset value corresponding thereto. The difference obtained in the operation unit reflects the consumption amount of the first portion at each position.

Moreover, the circuit board may include a communication device configured to wirelessly transmit the first digital value and the second digital value to the operation unit.

In yet another exemplary embodiment, a method of inspecting a focus ring with a measuring device configured to measure electrostatic capacitance is provided. The focus ring is provided on a mounting table configured to mount thereon a processing target object within a processing vessel of a plasma processing apparatus, and the focus ring has an annular plate-shaped first portion and an annular plate-shaped second portion which is extended on the first portion, and a diameter of an inner periphery of the second portion is larger than a diameter of an inner periphery of the first portion. The measuring device includes a base substrate having a disk shape, a sensor chip and a circuit board. The sensor chip has a sensor electrode and is provided along an edge of the base substrate. The circuit board is configured to output a high frequency signal to the sensor electrode and acquire a digital value indicating electrostatic capacitance based on a voltage amplitude in the sensor electrode. The method includes scanning the measuring device such that the sensor chip is moved on the first portion of the focus ring and within a region surrounded by the inner periphery of the second portion of the focus ring; and obtaining difference values at multiple positions along a direction which intersects with the inner periphery of the second portion of the focus ring by performing a difference operation with respect to the digital values acquired by the measuring device at the multiple positions. According to this method, it is possible to figure out the consumption amount of the first portion of the focus ring. The method may further include calculating a difference between each of the difference values and a preset value corresponding thereto.

In still yet another exemplary embodiment, a method of inspecting a focus ring with a measuring device configured to measure electrostatic capacitance is provided. The focus ring is provided on a mounting table configured to mount thereon a processing target object within a processing vessel of a plasma processing apparatus, and the focus ring has an annular plate-shaped first portion and an annular plate-shaped second portion which is extended on the first portion, and a diameter of an inner periphery of the second portion is larger than a diameter of an inner periphery of the first portion. The measuring device includes a base substrate having a disk shape, a sensor chip and a circuit board. The sensor chip has a first sensor electrode and a second sensor electrode. The first sensor electrode faces downwards and the second sensor electrode faces an outside of an edge of the base substrate. The sensor chip is provided along the edge of the base substrate. The circuit board is configured to output a high frequency signal to the first sensor electrode and the second sensor electrode and acquire a first digital value indicating electrostatic capacitance based on a voltage amplitude in the first sensor electrode and a second digital value indicating electrostatic capacitance based on a voltage amplitude in the second sensor electrode. The method includes scanning the measuring device such that the sensor chip is moved on the first portion of the focus ring and within a region surrounded by the inner periphery of the second portion of the focus ring; and obtaining difference values at multiple positions along a direction which intersects with the inner periphery of the second portion of the focus ring by performing a difference operation with respect to the first digital values acquired by the measuring device at the multiple positions. According to this method, it is possible to figure out the consumption amounts of the first portion and the second portion of the focus ring. The method may further include calculating a difference between each of the difference values and a preset value corresponding thereto.

As described above, according to the exemplary embodiments, it is possible to inspect the focus ring to figure out the consumption amount thereof.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

In the detailed description that follows, embodiments are described as illustrations only since various changes and modifications will become apparent to those skilled in the art from the following detailed description. The use of the same reference numbers in different figures indicates similar or identical items.

FIG. 15 is a flowchart for describing a method of inspecting a focus ring according to another exemplary embodiment;

FIG. 16 is a diagram illustrating an example of an arrangement position of a sensor chip to a base substrate; and FIG. 17 is a diagram illustrating another example of the arrangement position of the sensor chip to the base substrate.

DETAILED DESCRIPTION

Figure 1:
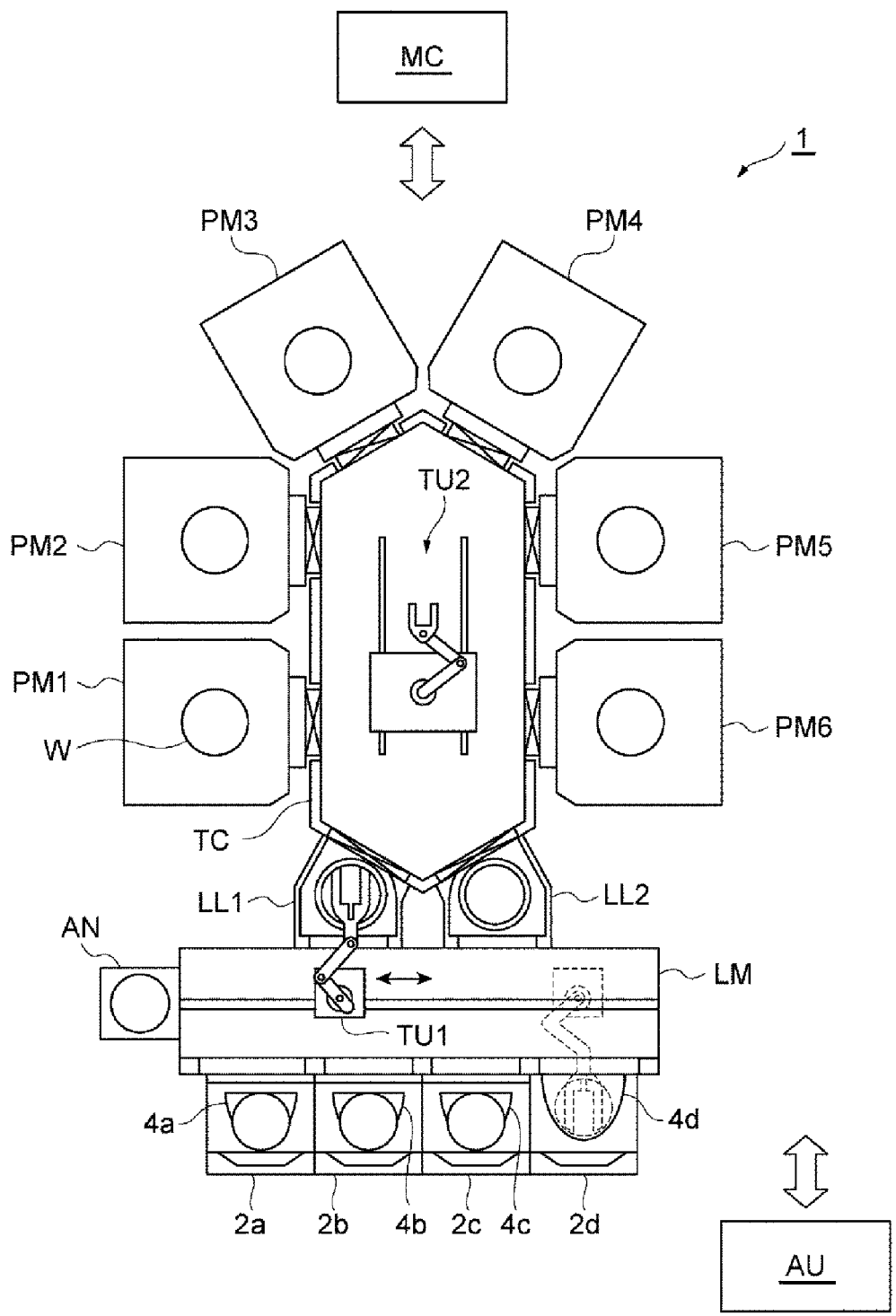
FIG. 1 is a diagram illustrating a system according to an exemplary embodiment.

In the following detailed description, reference is made to the accompanying drawings, which form a part of the description. In the drawings, similar symbols typically identify similar components, unless context dictates otherwise. Furthermore, unless otherwise noted, the description of each successive drawing may reference features from one or more of the previous drawings to provide clearer context and a more substantive explanation of the current exemplary embodiment. Still, the exemplary embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein and illustrated in the drawings, may be arranged, substituted, combined, separated, and designed in a wide variety of different configurations, all of which are explicitly contemplated herein.

FIG. 1 is a diagram illustrating a system according to an exemplary embodiment. The system shown in FIG. 1 includes a processing apparatus configured to process a processing target object (hereinafter, referred to as "wafer W") and a transfer device configured to transfer the processing target object into the processing apparatus, and is configured as a processing system 1 capable of inspecting a focus ring provided within a processing vessel of a plasma processing apparatus. The processing system 1 includes placing tables 2a to 2d, containers 4a to 4d, a loader module LM, an aligner AN, load lock chambers LL1 and LL2, process modules PM1 to PM6 and a transfer chamber TC.

The placing tables 2a to 2d are arranged along one side of the loader module LM. The containers 4a to 4d are mounted on the placing tables 2a to 2d, respectively. Each of the containers 4a to 4d is configured to accommodate wafers W therein.

The loader module LM includes a chamber wall that forms therein a transfer space which is maintained at an atmospheric pressure. The loader module LM has a transfer device TU1 within the transfer space. The transfer device TU1 is configured to transfer wafers W between the containers 4a to 4d and the aligner AN, between the aligner AN and the load lock chambers LL1 and LL2, and between the load lock chambers LL1 and LL2 and the containers 4a to 4d.

The aligner AN is connected to the loader module LM. The aligner AN is configured to perform position adjustment (position correction) of the wafer W. The position adjustment of the wafer W in the aligner AN may be performed by using an orientation flat or a notch of the wafer W.

The load lock chambers LL1 and the LL2 are provided between the loader module LM and the transfer chamber TC. Each of the load lock chamber LL1 and the load lock chamber LL2 is provided with a preliminary decompression room.

The transfer chamber TC is connected to the load lock chamber LL1 and the load lock chamber LL2 via respective gate valves. The transfer chamber TC is provided with a decompression room which can be decompressed, and a transfer device TU2 is accommodated in the decompression room. The transfer device TU2 is configured to transfer wafers W between the load lock chambers LL1, LL2 and the process modules PM1 to PM6 and between any two of the process modules PM1 to PM6.

The process modules PM1 to PM6 are connected to the transfer chamber TC via respective gate valves. Each of the process modules PM1 to PM6 is a processing apparatus configured to perform a preset process such as a plasma process on a wafer W.

A series of operations to perform the process on the wafer W in this processing system 1 is as follows, for example. The transfer device TU1 of the loader module LM takes out a wafer W from one of the containers 4a to 4d and transfers the wafer W into the aligner AN. Then, the transfer device TU1 takes out the wafer W, on which the position adjustment is performed, from the aligner AN and transfers the wafer W into one of the load lock chambers LL1 and LL2. Then, the corresponding load lock chamber decompresses the preliminary decompression room to a preset pressure. Thereafter, the transfer device TU2 of the transfer chamber TC takes out the wafer W from the corresponding load lock chamber and transfers the wafer W into one of the process modules PM1 to PM6. Here, at least one of the process modules PM1 to PM6 processes the wafer W. Afterwards, the transfer device TU2 transfers the processed wafer W from the corresponding process module into one of the load lock chambers LL1 and LL2. Then, the transfer device TU1 transfers the wafer W from the corresponding load lock chamber into one of the containers 4a to 4d.

The processing system 1 further includes a controller MC. The controller MC may be implemented by a computer including a processor, a storage device such as a memory, a display device, an input/output device, a communication device, and so forth. The controller MC controls the respective components of the processing system 1 according to a program stored in the storage device, so that the aforementioned series of operations of the processing system 1 are performed.

Figure 2:
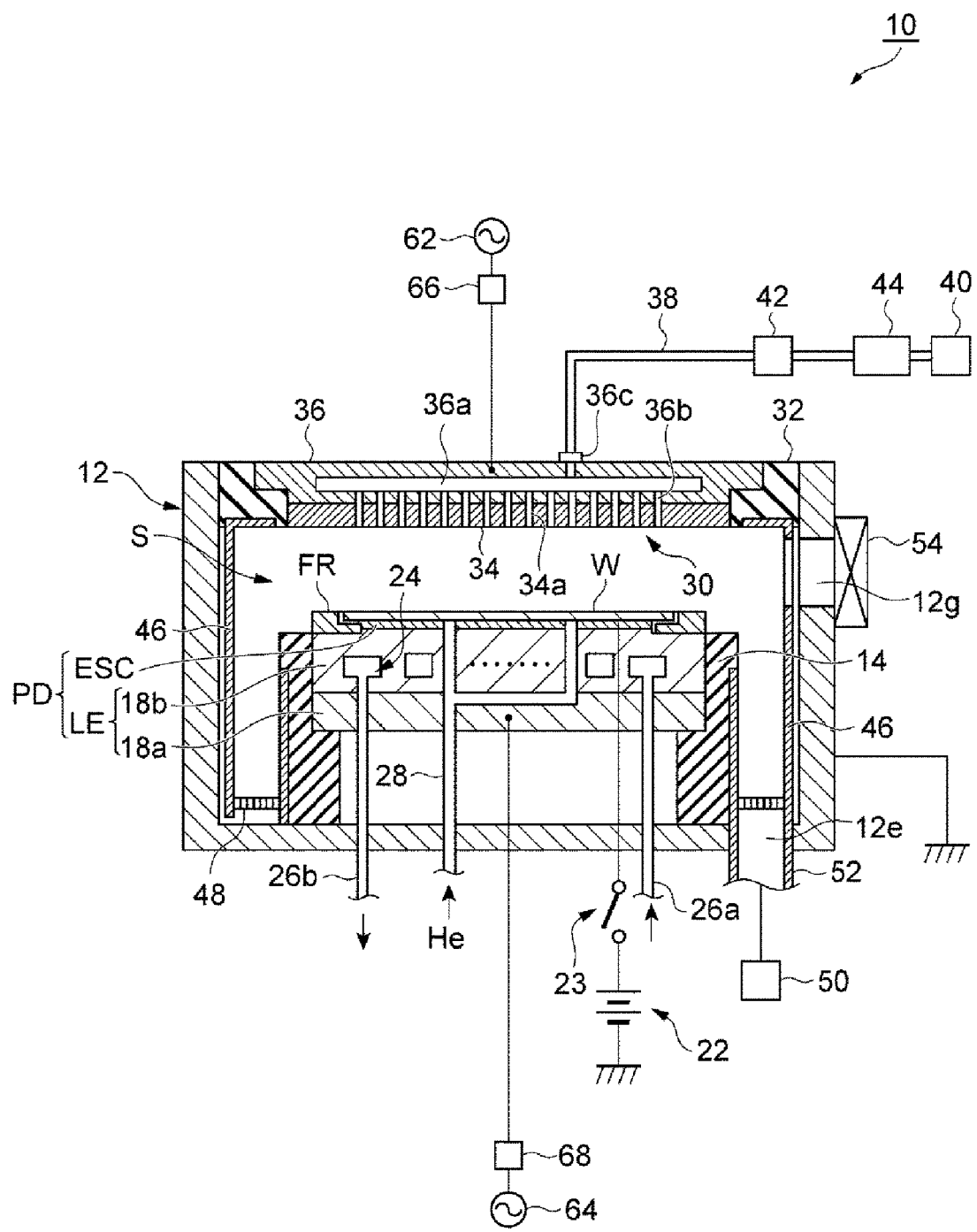
FIG. 2 is a diagram illustrating an example of a plasma processing apparatus.

FIG. 2 is a diagram illustrating an example of a plasma processing apparatus as one of the process modules PM1 to PM6. The plasma processing apparatus 10 shown in FIG. 2 is configured as a capacitively coupled plasma etching apparatus. The plasma processing apparatus 10 includes a substantially cylindrical processing vessel 12. The processing vessel 12 is made of, by way of non-limiting example, aluminum, and an inner wall surface of the processing vessel 12 may be anodically oxidized. The processing vessel 12 is frame-grounded.

A substantially cylindrical supporting member 14 is provided on a bottom portion of the processing vessel 12. The supporting member 14 is made of, by way of example, but not limitation, an insulating material. Within the processing vessel 12, the supporting member 14 is vertically extended from the bottom portion of the processing vessel 12. A mounting table PD is provided within the processing vessel 12. The mounting table PD is supported on the supporting member 14.

The mounting table PD includes a lower electrode LE and an electrostatic chuck ESC. The lower electrode LE includes a first plate 18a and a second plate 18b. Each of the first plate 18a and the second plate 18b is made of a metal such as, but not limited to, aluminum and has a substantially disk shape. The second plate 18b is provided on the first plate 18a and is electrically connected to the first plate 18a.

The electrostatic chuck ESC is provided on the second plate 18b. The electrostatic chuck ESC has a substantially disk shape, and includes a structure in which an electrode made of a conductive film is embedded between a pair of insulating layers or insulating sheets. The electrode of the electrostatic chuck ESC is electrically connected to a DC power supply 22 via a switch 23. The electrostatic chuck ESC is configured to attract and hold the wafer W by an electrostatic force such as a Coulomb force generated by a DC voltage applied from the DC power supply 22. Accordingly, the electrostatic chuck ESC is capable of holding the wafer W thereon.

Figure 3:
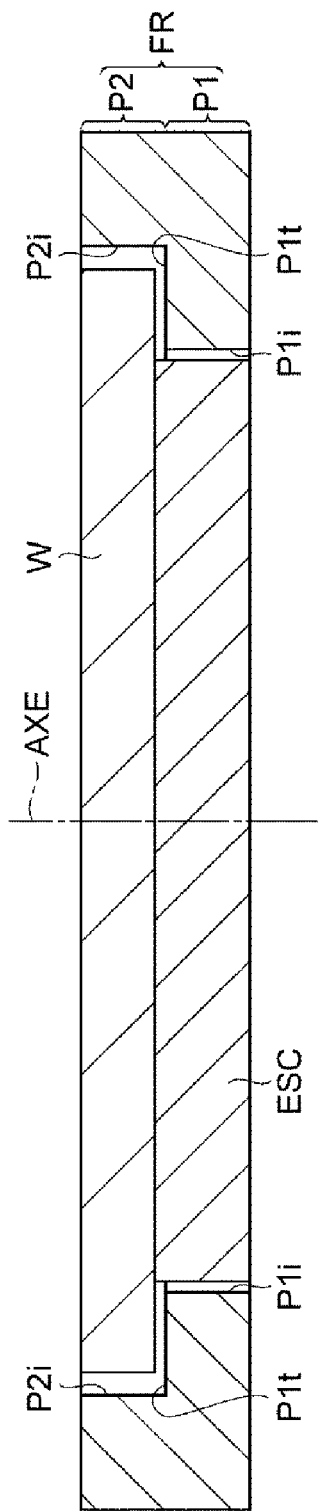
FIG. 3 is a cross sectional view illustrating a configuration of an electrostatic chuck and a focus ring.

A focus ring FR is provided on a peripheral portion of the second plate 18b. FIG. 3 is a cross sectional view illustrating a configuration of the electrostatic chuck and the focus ring. As depicted in FIG. 3, the focus ring FR is extended in a circumferential direction with respect to a central axis AXE of the electrostatic chuck ESC to surround an edge of the wafer W and the electrostatic chuck ESC. The focus ring FR includes a first portion P1 and a second portion P2. Each of the first portion P1 and the second portion P2 has an annular plate shape. The second portion P2 is provided on the first portion P1. An inner periphery P2i of the second portion P2 has a diameter larger than a diameter of an inner periphery P1i of the first portion P1. The wafer W is mounted on the electrostatic chuck ESC such that the edge region thereof is located above the first portion P1 of the focus ring FR. The focus ring FR may be made of any one of various materials such as silicon, silicon carbide, silicon oxide, etc.

Referring back to FIG. 2, a coolant path 24 is provided within the second plate 18b. The coolant path 24 constitutes a temperature control device. A coolant is supplied into the coolant path 24 from a chiller unit provided outside the processing vessel 12 via a pipeline 26a, and the coolant supplied into the coolant path 24 is returned back into the chiller unit via a pipeline 26b. With this configuration, the coolant is circulated between the coolant path 24 and the chiller unit. By controlling a temperature of the coolant, a temperature of the wafer W held on the electrostatic chuck ESC can be controlled.

Further, the plasma processing apparatus 10 is equipped with a gas supply line 28. Through the gas supply line 28, a heat transfer gas, for example, a He gas, is supplied from a heat transfer gas supply device into a gap between a top surface of the electrostatic chuck ESC and a rear surface of the wafer W.

Further, the plasma processing apparatus 10 includes an upper electrode 30. The upper electrode 30 is provided above the mounting table PD, facing the mounting table PD. Formed between the upper electrode 30 and the mounting table PD is a processing space S in which a plasma process is performed on the wafer W.

The upper electrode 30 is supported at an upper portion of the processing vessel 12 with an insulating shield member 32 therebetween. The upper electrode 30 may include a ceiling plate 34 and a supporting body 36. The ceiling plate 34 directly faces the processing space S and is provided with a multiple number of gas discharge holes 34a. The ceiling plate 34 may be formed of silicon or quartz. Alternatively, the ceiling plate 34 may be fabricated by forming a plasma-resistance film of, but not limited to, yttrium oxide on a surface of a substrate member which is made of aluminum.

The supporting body 36 is configured to support the ceiling plate 34 in a detachable manner, and is made of a conductive material such as, but not limited to, aluminum. The supporting body 36 may have a water-cooling structure. A gas diffusion space 36a is formed within the supporting body 36. A multiple number of gas through holes 36b is extended downwards from the gas diffusion space 36a, and these gas through holes 36b communicate with the gas discharge holes 34a, respectively. Further, the supporting body 36 is also provided with a gas inlet opening 36c through which a processing gas is introduced into the gas diffusion space 36a, and this gas inlet opening 36c is connected to a gas supply line 38.

The gas supply line 38 is connected to a gas source group 40 via a valve group 42 and a flow rate controller group 44. The gas source group 40 includes a plurality of gas sources. The valve group 42 includes a multiple number of valves, and the flow rate controller group 44 includes a multiple number of flow rate controllers such as mass flow controllers. Each of the gas sources belonging to the gas source group 40 is connected to the gas supply line 38 via each corresponding valve belonging to the valve group 42 and each corresponding flow rate controller belonging to the flow rate controller group 44.

Further, in the plasma processing apparatus 10, a deposition shield 46 is provided along an inner wall of the processing vessel 12 in a detachable manner. The deposition shield 46 is also provided on an outer side surface of the supporting member 14. The deposition shield 46 is configured to suppress an etching byproduct (deposit) from adhering to the processing vessel 12, and is formed by coating an aluminum member with ceramics such as $Y_2O_3$.

At the bottom portion side of the processing vessel 12, a gas exhaust plate 48 is provided between the supporting member 14 and a side wall of the processing vessel 12. The gas exhaust plate 48 may be made of, by way of example, an aluminum member coated with ceramic such as $Y_2O_3$. The gas exhaust plate 48 is provided with a multiple number of through holes in a plate thickness direction thereof. The processing vessel 12 is also provided with a gas exhaust opening 12e under the gas exhaust plate 48, and the gas exhaust opening 12e is connected with a gas exhaust device 50 via a gas exhaust line 52. The gas exhaust device 50 includes a pressure control valve and a vacuum pump such as a turbo molecular pump, and is capable of decompressing the space within the processing vessel 12 to a required pressure level. Further, a carry-in/out opening 12g for the wafer W is provided at the side wall of the processing vessel 12, and the carry-in/out opening 12g is opened or closed by a gate valve 54.

Furthermore, the plasma processing apparatus 10 includes a first high frequency power supply 62 and a second high frequency power supply 64. The first high frequency power supply 62 is configured to generate a high frequency power for plasma generation having a frequency in the range from, for example, 27 MHz to 100 MHz. The first high frequency power supply 62 is connected to the upper electrode 30 via a matching device 66. The matching device 66 includes a circuit configured to match an output impedance of the first high frequency power supply 62 and an input impedance at a load side (upper electrode 30). Further, the first high frequency power supply 62 may be connected to the lower electrode LE via the matching device 66.

The second high frequency power supply 64 is configured to generate a high frequency bias power for attracting ions into the wafer W. For example, the second high frequency power supply 64 generates the high frequency bias power having a frequency in the range from 400 kHz to 13.56 MHz. The second high frequency power supply 64 is connected to the lower electrode LE via a matching device 68. The matching device 68 includes a circuit configured to match an output impedance of the second high frequency power supply 64 and an input impedance at a load side (lower electrode LE).

In the plasma processing apparatus 10 having the above-described configuration, a gas from one or more gas sources selected from the gas sources is supplied into the processing vessel 12. Further, a pressure in the space within the processing vessel 12 is set to a preset pressure by the gas exhaust device 50. The gas within the processing vessel 12 is excited by the high frequency power from the first high frequency power supply 62, so that plasma is generated, and the wafer W is processed by generated active species. Further, when necessary, ions may be attracted into the wafer W by the high frequency bias power from the second high frequency power supply 64.

Figure 4:
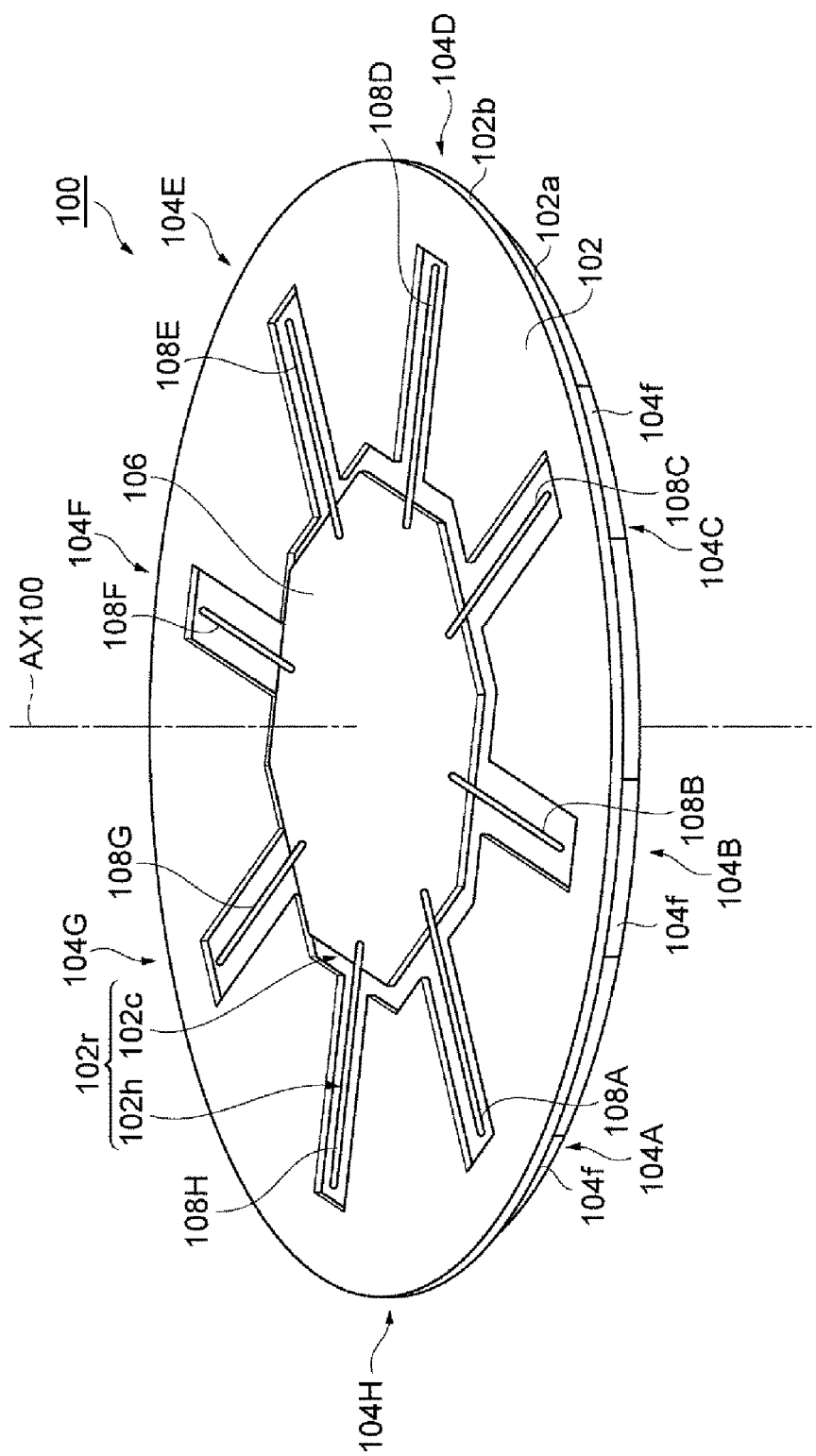
FIG. 4 is a perspective view of a measuring device according to the exemplary embodiment.

Now, an exemplary embodiment of a measuring device used to inspect the focus ring FR in the processing system 1 will be explained. FIG. 4 is a perspective view of the measuring device according to the exemplary embodiment. The measuring device 100 shown in FIG. 4 has a base substrate 102. The base substrate 102 is made of, by way of non-limiting example, silicon and has a substantially disk shape, the same as the wafer W.

The base substrate 102 has a lower portion 102a and an upper portion 102b. The lower portion 102a is located closer to the electrostatic chuck ESC than the upper portion 102b when the measuring device 100 is placed on the electrostatic chuck ESC. A plurality of sensor chips 104A to 104H configured to measure the electrostatic capacitance is provided at the lower portion 102a of the base substrate 102. The number of the sensor chips mounted to the measuring device 100 may be one or more. The sensor chips 104A to 104H are arranged at a regular interval along an edge of the base substrate 102, for example, along the entire circumference of the edge of the base substrate 102. To be specific, the sensor chips 104A to 104H are provided such that front end faces 104f thereof are arranged along the edge of the lower portion 102a of the base substrate 102. In FIG. 4, among the sensor chips 104A to 104H, only the sensor chips 104A to 104C are depicted.

A top surface of the upper portion 102b of the base substrate 102 is provided with a recess 102r. The recess 102r includes a central region 102c and a plurality of radial regions 102h. The central region 102c intersects with a central axis AX100. The central axis AX100 is an axis that passes through a center of the base substrate 102 in a thickness direction thereof. A circuit board 106 is provided at the central region 102c. The radial regions 102h are extended in radial directions with respect to the central axis AX100 from the central region 102c up to above regions where the sensor chips 104A to 104H are provided. Provided in the radial regions 102h is a plurality of wiring units 108A to 108H which are configured to electrically connect the sensor chips 104A to 104H to the circuit board 106, respectively. In the measuring device 100 of FIG. 4, the sensor chips 104A to 104H are shown to be mounted to the lower portion 102a of the base substrate 102. Alternatively, however, the sensor chips 104A to 104H may be mounted to the upper portion 102b of the base substrate 102.

Figure 5:
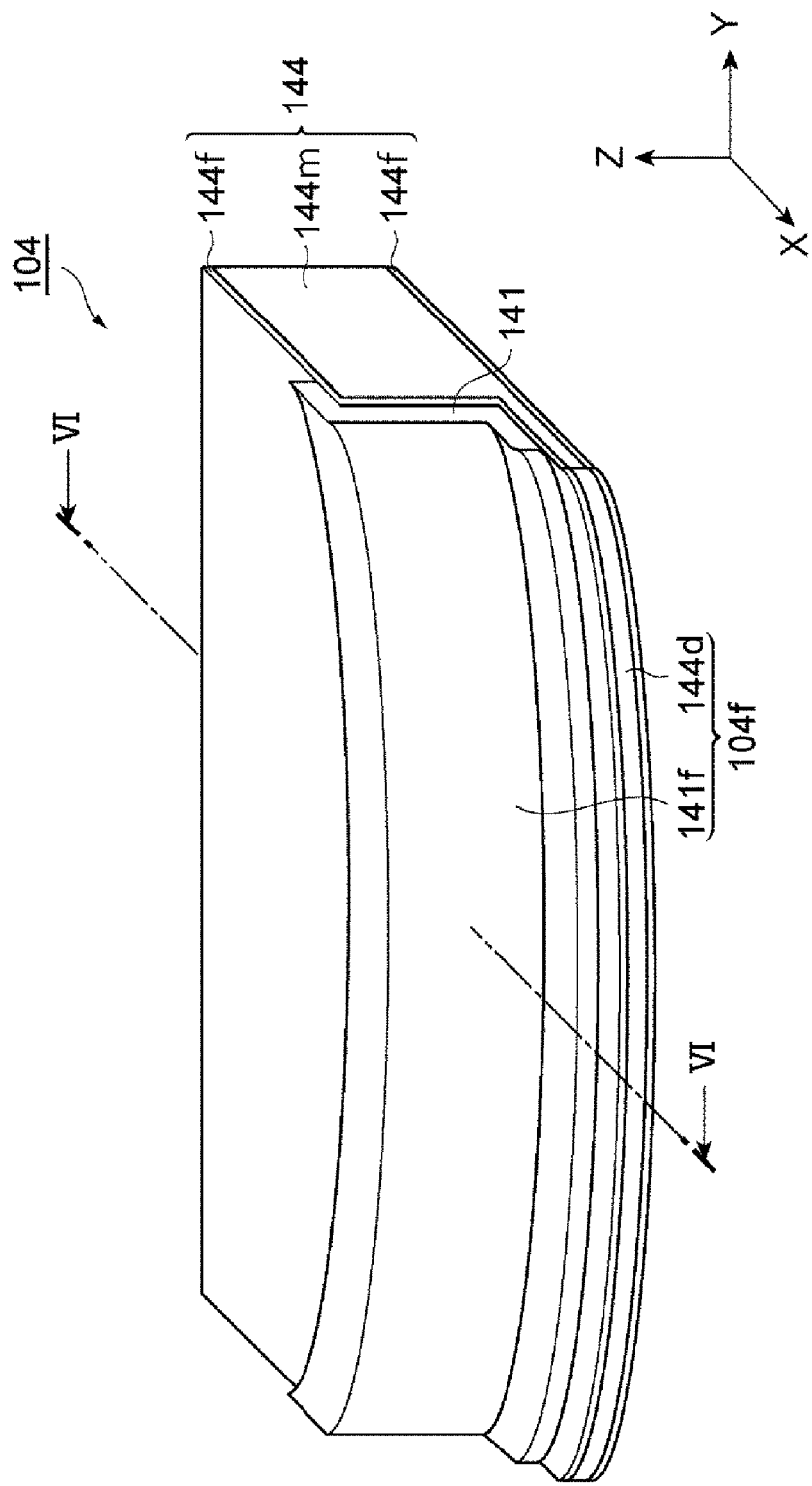
FIG. 5 is a perspective view of a sensor chip according to the exemplary embodiment.
Figure 6:
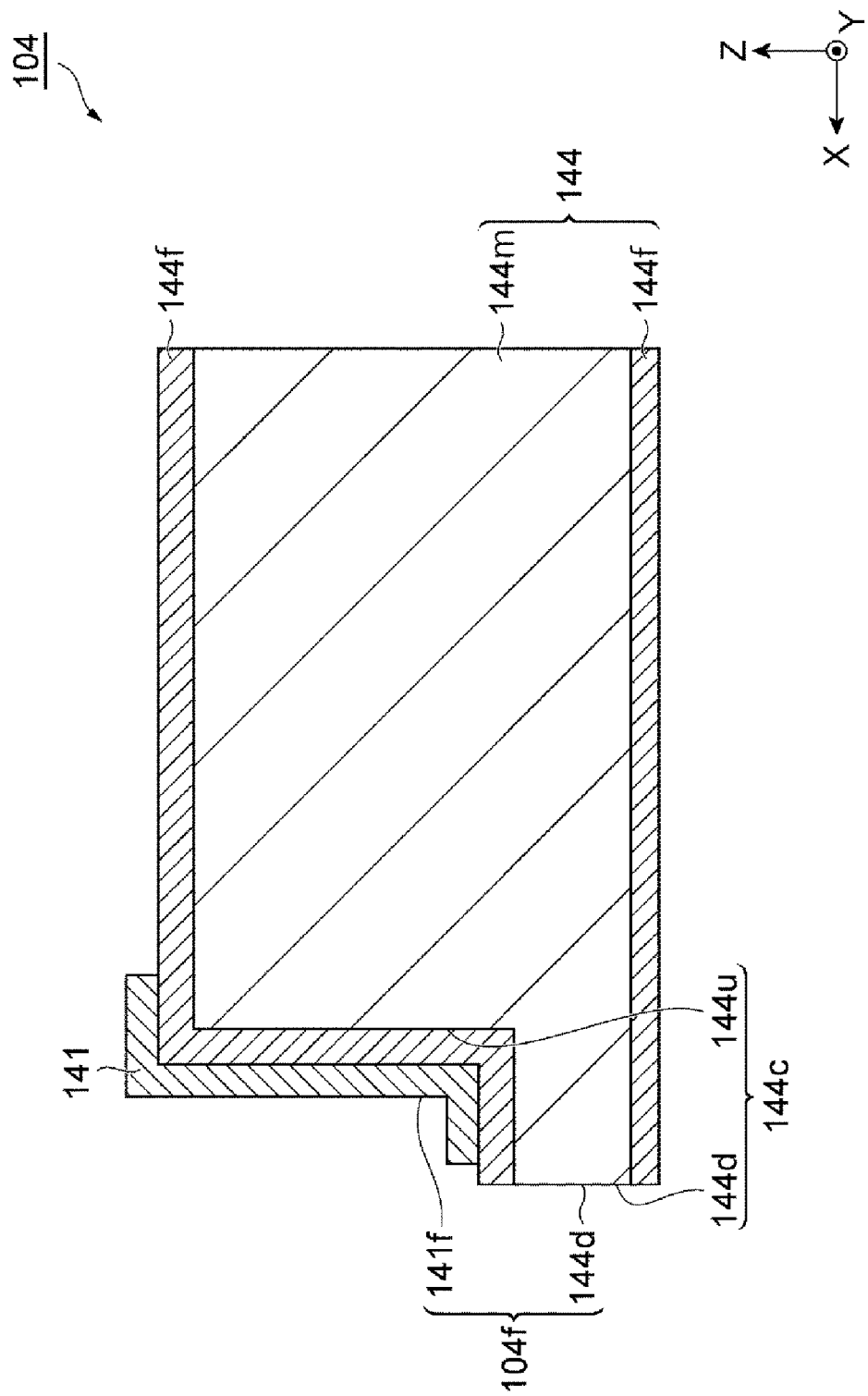
FIG. 6 is a cross sectional view taken along a line VI-VI of FIG. 5.

Hereinafter, a sensor chip will be elaborated. FIG. 5 is a perspective view illustrating a sensor chip according to the exemplary embodiment. FIG. 6 is a cross sectional view taken along a line VI-VI of FIG. 5. A sensor chip 104 depicted in FIG. 5 and FIG. 6 is a sensor chip used as the sensor chips 104A to 104H of the measuring device 100. Further, the following description will be provided with reference to an XYZ orthogonal coordinates system appropriately. The X direction represents a front direction of the sensor chip 104; the Y direction, a width direction of the sensor chip 104 as one direction orthogonal to the X direction; and the Z direction, an upward direction of the sensor chip 104 orthogonal to the X direction and the Y direction.

As shown in FIG. 5 and FIG. 6, the sensor chip 104 is equipped with a sensor electrode 141 and a substrate member 144. The substrate member 144 includes a main body 144m and a surface member 144f. The main body 144m is made of, by way of non-limiting example, silicon. The surface member 144f is an insulating region and is provided on a surface of the main body 144m. By way of non-limiting example, the surface member 144f is a thermal oxide film of silicon.

A surface of the substrate member 144 includes a front end face 144c. The front end face 144c has a step shape and includes an upper portion 144u and a lower portion 144d. The lower portion 144d of the front end face 144c is protruded forward more than the upper portion 144u of the front end face 144c. In the exemplary embodiment, the upper portion 144u and the lower portion 144d of the front end face 144c are curved surfaces having preset curvatures. That is, the upper portion 144u of the front end face 144c has a constant curvature at certain positions on the upper portion 144u, and the curvature of the upper portion 144u is a reciprocal of a distance between the central axis AX100 of the measuring device 100 and the upper portion 144u of the front end face 144c. Further, the lower portion 144d of the front end face 144c has a constant curvature at certain positions on the lower portion 144d, and the curvature of the lower portion 144d is a reciprocal of a distance between the central axis AX100 of the measuring device 100 and the lower portion 144d of the front end face 144c.

The sensor electrode 141 is provided along the upper portion 144u of the front end face 144c. In the exemplary embodiment, a front face 141f of this sensor electrode 141 is also formed as a curved surface. That is, the front face 141f of the sensor electrode 141 has a constant curvature at certain positions on the front face 141f, and the curvature of the front face 141f is a reciprocal of a distance between the central axis AX100 of the measuring device 100 and the front face 141f.

The front end face 104f of the sensor chip 104 includes the lower portion 144d of the front end face 144c of the substrate member 144 and the front face 141f of the sensor electrode 141. The sensor chip 104 is mounted to the base substrate 102 such that the front end face 104f thereof is located along the edge (circumference) of the base substrate 102. That is, the sensor chip 104 is mounted to the base substrate 102 such that a center of curvature of the lower portion of the front end face 144c of the substrate member 144 and a center of curvature of the front face 141f of the sensor electrode 141 coincide with the central axis AX100.

Figure 7:
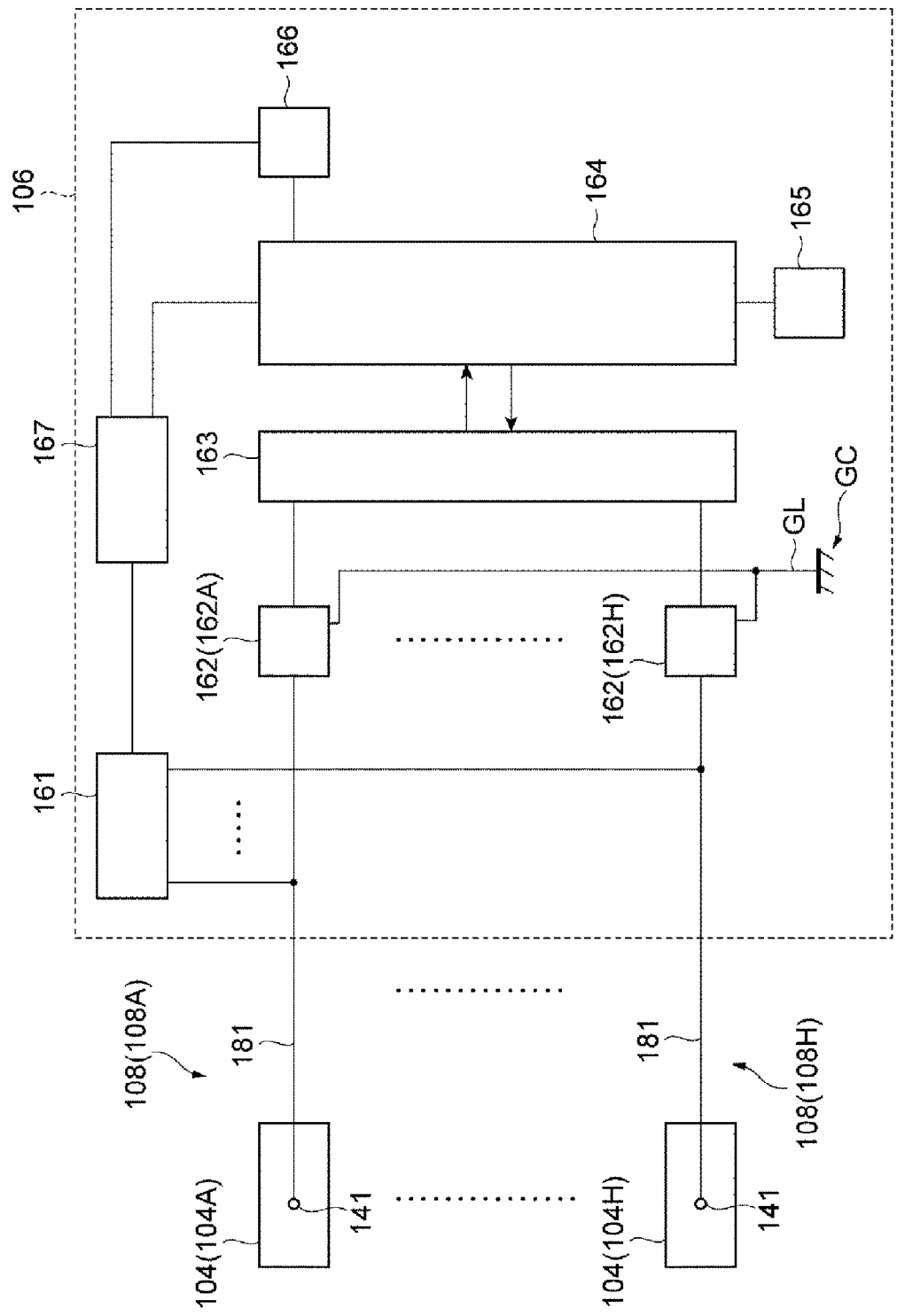
FIG. 7 is a diagram illustrating a configuration of a circuit board according to the exemplary embodiment.

The sensor electrode 141 of the sensor chip 104 is connected to the circuit board 106 via a wiring unit. FIG. 7 is a diagram illustrating a configuration of the circuit board according to the exemplary embodiment. As depicted in FIG. 7, the circuit board 106 includes a high frequency oscillator 161, a multiple number of C/V conversion circuits 162A to 162H and an A/D converter 163. In the exemplary embodiment, the circuit board 106 may further include a storage device 165 and a communication device 166. Further, in another exemplary embodiment, the circuit board 106 may further include a processor 164 and a power supply 167.

Each of the sensor chips 104A to 104H is connected to the circuit board 106 via each corresponding one of the wiring units 108A to 108H. Further, each of the sensor chips 104A to 104H is connected to each corresponding one of the C/V conversion circuits 162A to 162H via some wirings belonging to each corresponding one of the wiring units. Hereinafter, a single sensor chip 104 having the same configuration as each of the sensor chips 104A to 104H, a single wiring unit 108 having the same configuration as each of the wiring units 108A to 108H and a single C/V conversion circuit 162 having the same configuration as each of the C/V conversion circuits 162A to 162H will be explained.

The wiring unit 108 includes a wiring 181. The wiring 181 is connected to the sensor electrode 141. The high frequency oscillator 161 is connected to a power supply 167 such as a battery, and is configured to generate a high frequency signal by receiving a power from the power supply 167. Further, the power supply 167 is also connected to the processor 164 and the communication device 166. The high frequency oscillator 161 has an output line. The high frequency oscillator 161 is configured to output the generated high frequency signal to the wiring 181 via the output line. Accordingly, the high frequency signal from the high frequency oscillator 161 is output to the sensor electrode 141 of the sensor chip 104.

The wiring 181 is connected to an input terminal of the C/V conversion circuit 162. That is, the sensor electrode 141 of the sensor chip 104 is connected to the input terminal of the C/V conversion circuit 162. Further, a ground potential line GL connected to a ground GC is also coupled to the C/V conversion circuit 162. The C/V conversion circuit 162 is configured to generate, based on a voltage amplitude at the input terminal thereof, a voltage signal indicating electrostatic capacitance formed by the sensor electrode connected to the input terminal, and output the generated voltage signal. Further, as the electrostatic capacitance formed by the sensor electrode 141 connected to the C/V conversion circuit 162 increases, the magnitude of the voltage of the voltage signal output from the C/V conversion circuit 162 also increases.

Output terminals of the C/V conversion circuits 162A to 162H are connected to an input terminal of the A/D converter 163. Further, the A/D converter 163 is connected to the processor 164. The A/D converter 163 is controlled by a control signal from the processor 164, and is configured to convert the output signals (voltage signals) of the C/V conversion circuits 162A to 162H to digital values. That is, the A/D converter 163 is configured to generate a digital value indicating the magnitude of the electrostatic capacitance and output the digital value to the processor 164.

The processor 164 is connected to the storage device 165. The storage device 165 is implemented by, by way of non-limiting example, a nonvolatile memory and is configured to store therein the digital values output from the A/D converter 163.

The communication device 166 follows the wireless communication standards. For example, the communication device 166 is based on Bluetooth (registered trademark). The communication device 166 is configured to wirelessly transmit the digital values stored in the storage device 165.

Referring back to FIG. 1, the processing system 1 inspects the focus ring FR within a plasma processing apparatus employed as one of the process modules PM1 to PM6 by using the measuring device 100. During the inspection of the focus ring FR, the measuring device 100 is scanned within a region surrounded by the focus ring FR with the transfer device TU2. Multiple digital values acquired during the scanning of the measuring device 100 are sent to an operation unit AU of the processing system 1. The operation unit AU is implemented by a computer including a processor, a storage device such as a memory and a communication device, and is configured to perform an operation process on the multiple digital values to figure out a consumption amount of the focus ring FR. The operation process of the operation unit AU may be performed by the processor which is operated according to a program stored in the storage device of the operation unit AU.

Figure 8:
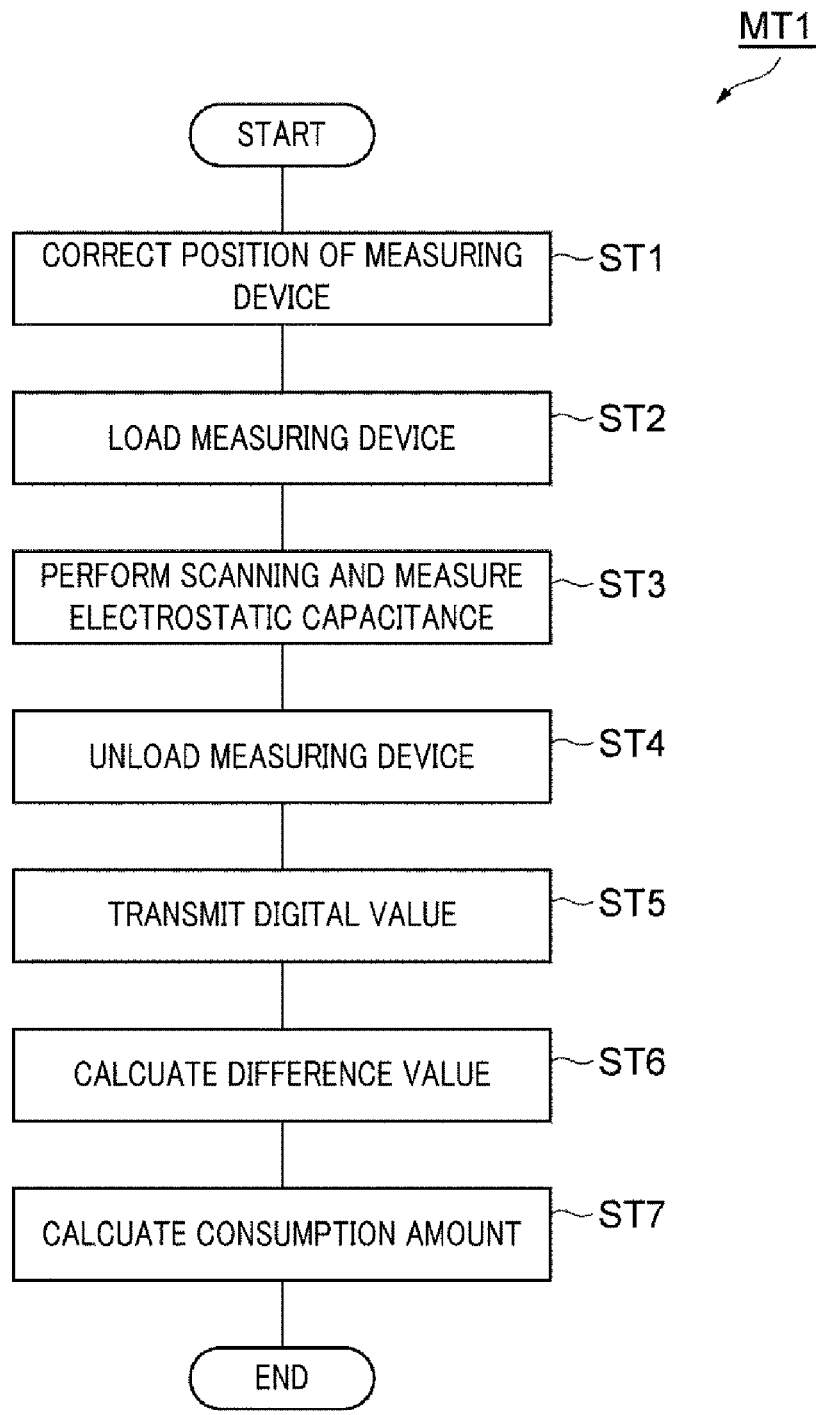
FIG. 8 is a flowchart for describing a method of inspecting the focus ring according to the exemplary embodiment.

Hereinafter, a method of inspecting the focus ring FR and operations of the individual components of the processing system 1 in performing the method according to the exemplary embodiment will be discussed. FIG. 8 is a flowchart for describing the method of inspecting the focus ring according to the exemplary embodiment.

In a method MT1 described in FIG. 8, the measuring device 100 accommodated in one of the containers 4a to 4d is carried into the aligner AN by the transfer device TU1. Then, in a process ST1, the position adjustment (position correction) of the measuring device 100 is performed by the aligner AN.

In a subsequent process ST2, the measuring device 100 is transferred into the plasma processing apparatus employed as one of the process modules PM1 to PM6. To elaborate, the measuring device 100 is transferred into one of the load lock chamber LL1 and the load lock chamber LL2 by the transfer device TU1. Subsequently, the measuring device 100 is transferred from the corresponding load lock chamber into the processing vessel of the plasma processing apparatus by the transfer device TU2.

In a subsequent process ST3, the measuring device 100 is scanned by the transfer device TU2. To elaborate, the transfer device TU2 scans the measuring device 100 such that the sensor chips 104A to 104H are moved on the first portion P1 of the focus ring FR and within a region surrounded by the inner periphery P2i of the second portion P2 of the focus ring. While the measuring device 100 is scanned, the measuring device 100 acquires a digital value indicating electrostatic capacitance based on a voltage amplitude of the sensor electrode 141. Then, the measuring device 100 stores multiple digital values obtained while the measuring device 100 is scanned in the storage device 165. Further, the multiple digital values may be acquired at preset timings under the control of the processor 164.

In a subsequent process ST4, the measuring device 100 is taken out from the process module and returned back into one of the containers 4a to 4d. In a subsequent process ST5, the digital values stored in the storage device 165 are sent to the operation unit AU. The digital values may be transmitted from the communication device 166 to the operation unit AU in response to an instruction from the operation unit AU, or may be transmitted to the operation unit AU at preset timing under the control of the processor 164 based on a count of a timer provided at the circuit board 106.

In a subsequent process ST6, the operation unit AU performs a difference operation with respect to the multiple digital values obtained by the measuring device 100 at multiple positions in a direction which intersects with the inner periphery P2*i* of the second portion P2 of the focus ring FR. Through this difference operation, the operation unit AU obtains multiple difference values at the multiple positions. The difference values at the multiple positions are defined by the following expression (1).

$$\Delta C(L(i)) = C(L(i)) - C(L(i-1)) \quad (1)$$

Here, i denotes an integer ranging from 1 to N. L(i) is a parameter indicating a preset position along the direction which intersects with the inner periphery P2*i* of the second portion P2 of the focus ring FR. Specifically, L(i) denotes a distance between the preset position and the inner periphery P2*i* of the second portion P2 of the focus ring FR. The smaller the value of i is, the larger the value of L(i) becomes. C(L(i)) indicates a digital value (electrostatic capacitance) acquired at the position specified by L(i). Further, a preset value may be used as C(L(0)). Alternatively, a value obtained by extrapolation using all or some of the multiple digital values may be used as C(L(0)).

According to the exemplary embodiment, in a subsequent process ST7, the operation unit AU calculates differences between multiple preset values and the multiple difference values at the multiple positions. Here, the multiple preset values are multiple difference values calculated from multiple digital values obtained at the multiple positions for the focus ring FR in an initial state where the focus ring is not consumed (worn), and may be previously stored in the storage device of the operation unit AU.

The electrostatic capacitance obtained from the voltage amplitude of the sensor electrode 141 increases as the sensor electrode 141 approaches the inner periphery P2*i* of the second portion P2 of the focus ring FR. Further, the degree of this increment decreases if the top face P1*t* of the first portion P1 of the focus ring FR is consumed (worn). Accordingly, the multiple difference values at the multiple positions, which are obtained by performing the difference operation with respect to the multiple digital values indicating the electrostatic capacitances at the multiple positions on the first portion P1, reflect the consumption amounts of the first portion P1 at the multiple positions. Thus, according to the processing system 1 and the method MT1, it is possible to figure out the consumption amount of the first portion P1 of the focus ring FR.

Furthermore, according to the exemplary embodiment, the differences between the multiple preset values and the multiple difference values at the multiple positions are calculated in the process ST7. The differences thus calculated reflect the consumption amounts of the first portion P1 at the respective positions. Thus, according to the processing system 1 and the method MT1, it is possible to figure out the consumption amount of the first portion P1 of the focus ring FR.

Figure 9:
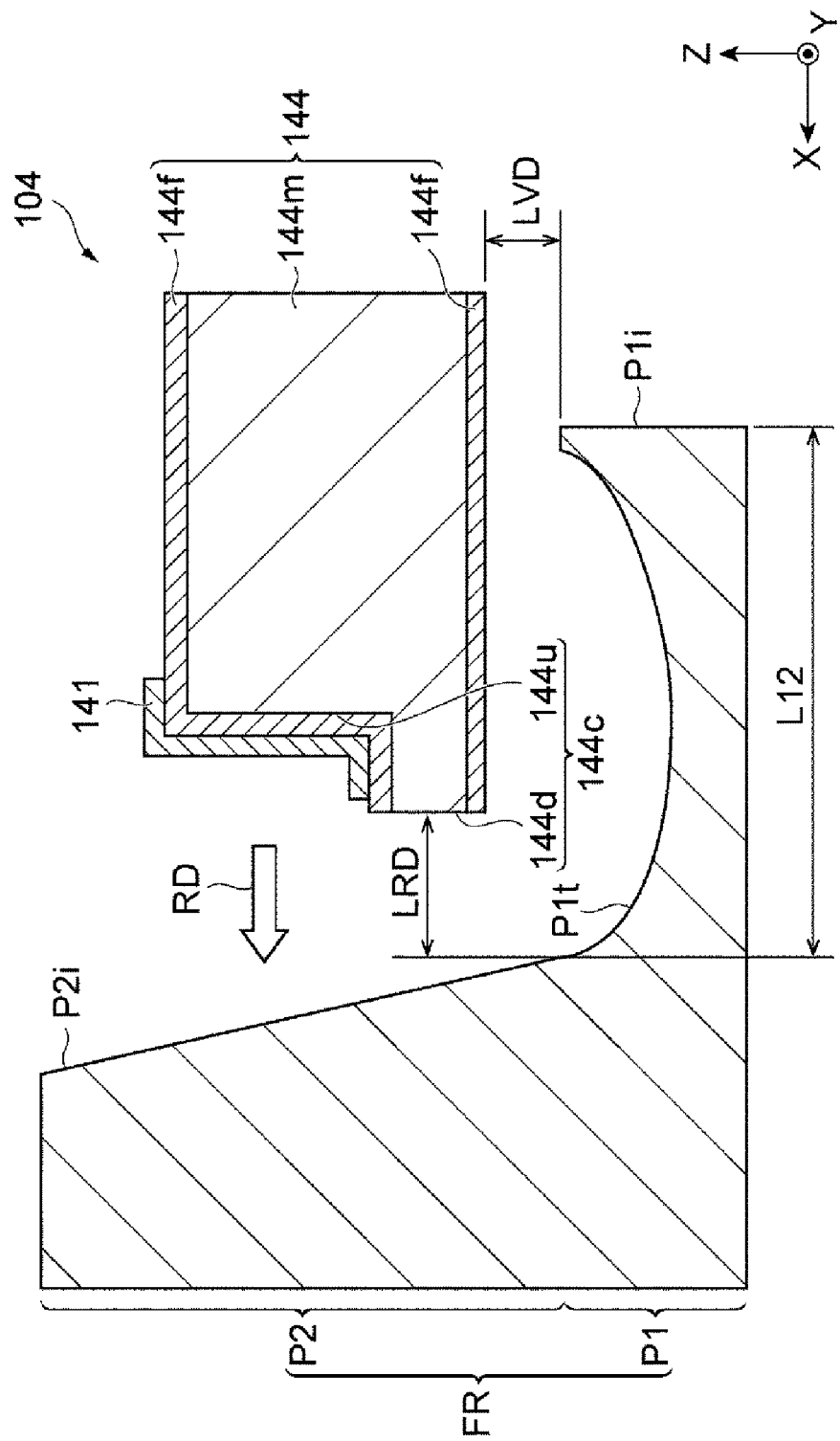
FIG. 9 is a diagram for describing an experiment.

Here, an experiment conducted by using the sensor chip 104 will be explained. In this experiment, as shown in FIG. 9, a consumed (worn) focus ring FR is used, and the sensor chip 104 is scanned in a direction RD toward the inner periphery P2*i* of the second portion P2 of the focus ring FR. Then, the electrostatic capacitances are measured at multiple positions along the direction RD by an electrostatic capacitance meter connected to the sensor electrode 141 of the sensor chip 104. Further, a distance LVD (in the Z direction) between a topmost position of the top face P1*t* of the first portion P1 of the focus ring FR and the bottom face of the sensor chip 104 is 100 μm. Furthermore, a distance L12 (shortest distance) between the inner periphery P1*i* of the first portion P1 and the inner periphery P2*i* of the second portion P2 is 2.5 mm.

Figure 10:
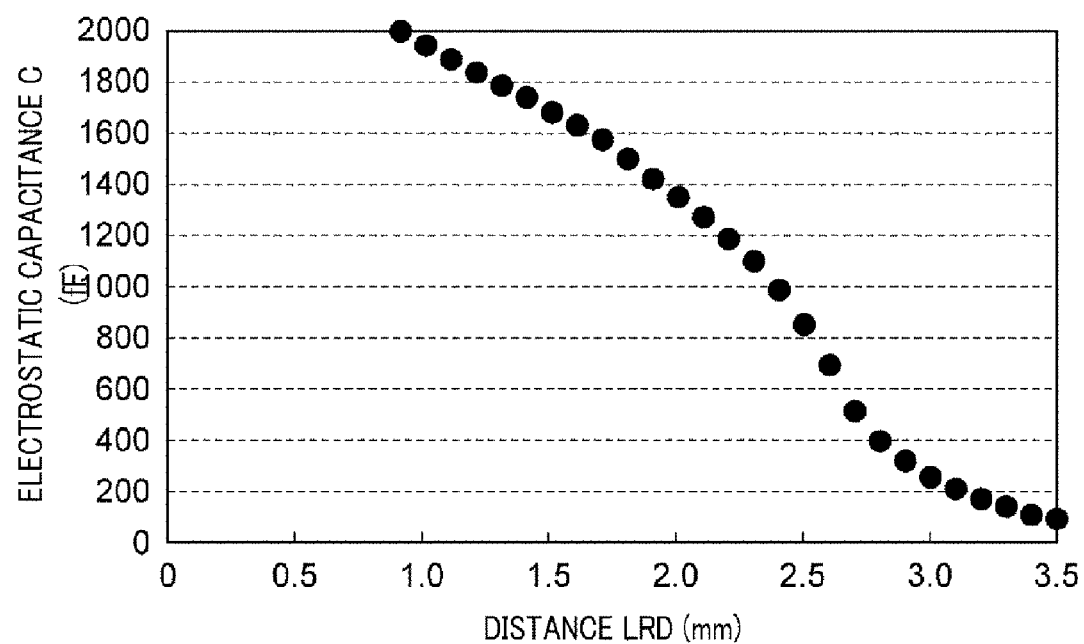
FIG. 10 is a graph showing electrostatic capacitance measured in the experiment.

A graph of FIG. 10 shows a relationship between the measured electrostatic capacitance and the distance LRD between the inner periphery P2*i* of the second portion P2 of the focus ring FR and the sensor chip 104. Further, the distance LRD is a distance between a boundary between the inner periphery P2*i* of the second portion P2 of the focus ring FR and the top face P1*t* of the first portion P1 and the lower portion 144*d* of the front end face 144*c* of the substrate member 144 of the sensor chip 104 in the direction RD. As depicted in FIG. 10, if the distance LRD becomes 2.5 mm, that is, if the sensor electrode 141 is located on the focus ring FR, the electrostatic capacitance is found to be increased rapidly. If the focus ring FR has not been consumed (worn), the electrostatic capacitance may be increased in a substantially linear manner as the sensor chip 104 approaches the inner periphery P2*i* of the second portion P2 with the distance LRD equal to or lower than 2.5 mm. Since, however, the focus ring FR used in the experiment is consumed (worn) as illustrated in FIG. 9, the degree of increment of the electrostatic capacitance with the approach of the sensor chip 104 toward the inner periphery P2*i* of the second portion P2 is found to be reduced, as compared to the linear increase.

Figure 11:
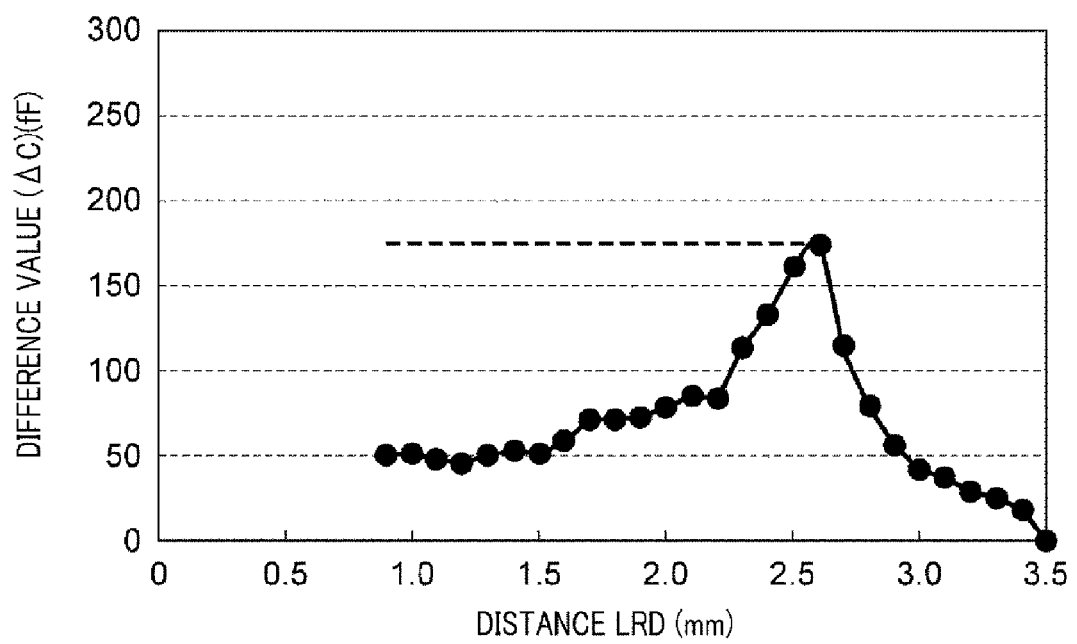
FIG. 11 is a graph showing a difference value of the electrostatic capacitance shown on the graph of FIG. 10.

A graph of FIG. 11 shows the difference value of the electrostatic capacitance shown in FIG. 10. The difference value (ΔC(LRD(i))) in FIG. 11 is calculated by using the following expression (2).

$$\Delta C(LRD(i)) = C(LRD(i)) - C(LRD(i-1)) \quad (2)$$

Here, i denotes an integer ranging from 1 to N. LRD(i) is a distance LRD at which each of multiple electrostatic capacitances is obtained. The smaller the value of i is, the larger the value of the distance LRD(i) becomes. Further, C(LRD(i)) denotes the electrostatic capacitance obtained at the distance LRD(i). Further, the same value as C(LRD(1)) is used as C(LRD(0)).

As shown in the graph of FIG. 11, a relationship between the distance LRD(i) and the multiple difference values reflects the shape of the top face P1*t* of the first portion P1 of the focus ring FR shown in FIG. 9. That is, the multiple difference values reflect the consumption amounts of the first portion at the multiple positions along the direction RD. Further, FIG. 11 depicts a dashed line indicating the multiple difference values obtained when the focus ring FR is not consumed (worn). That is, the dashed line indicates the multiple preset values at the multiple positions along the direction RD. As can be clearly seen from FIG. 11, the difference between the preset value and the difference value ΔC at each position reflects the consumption amount of the top face P1*t* of the first portion P1 of the focus ring FR of FIG. 9 in the Z direction. As proved from this experiment, according to the processing system 1 and the method MT1, it is possible to figure out the consumption amount of the first portion P1 of the focus ring FR.

Figure 12:
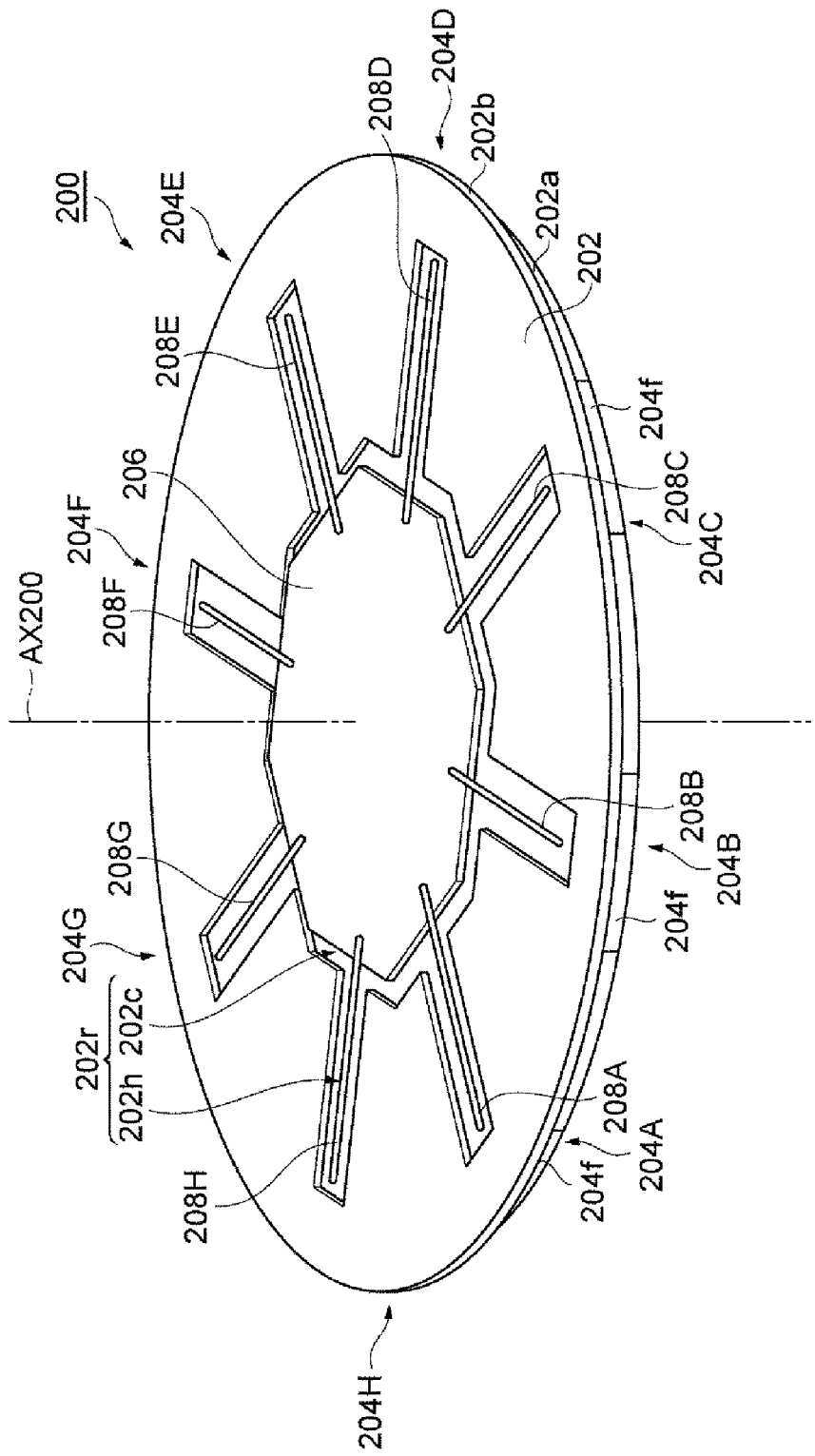
FIG. 12 is a perspective view illustrating a measuring device according to another exemplary embodiment.

Below, a measuring device 200 according to another exemplary embodiment will be explained. FIG. 12 is a perspective view of the measuring device according to another exemplary embodiment. The measuring device shown in FIG. 12 has a base substrate 202. The base substrate 202 is made of, by way of non-limiting example, silicon, and has a substantially disk shape, the same as the wafer W.

The base substrate 202 has a lower portion 202*a* and an upper portion 202*b*. The lower portion 202*a* is located closer to the electrostatic chuck ESC than the upper portion 202*b* when the measuring device 200 is placed on the electrostatic chuck ESC. A plurality of sensor chips 204A to 204H is provided at the lower portion 202*a* of the base substrate 202. The number of the sensor chips mounted to the measuring device 200 may be one or more. The sensor chips 204A to 204H are arranged at a regular interval along an edge of the base substrate 202, for example, along the entire circumference of the edge of the base substrate 202. To be specific, the sensor chips 204A to 204H are provided such that front end faces 204*f* thereof are arranged along the edge of the lower portion 202*a* of the base substrate 202. In FIG. 12, among the sensor chips 204A to 204H, only the sensor chips 204A to 204C are depicted.

A top surface of the upper portion 202*b* of the base substrate 202 is provided with a recess 202*r*. The recess 202*r* includes a central region 202*c* and a plurality of radial regions 202*h*. The central region 202*c* intersects with a central axis AX200. The central axis AX200 is an axis that passes through a center of the base substrate 202 in a thickness direction thereof. A circuit board 206 is provided at the central region 202*c*. The radial regions 202*h* are extended in radial directions with respect to the central axis AX200 from the central region 202*c* up to above regions where the sensor chips 204A to 204H are provided. Provided in the radial regions 202*h* is a plurality of wiring units 208A to 208H which are configured to electrically connect the sensor chips 204A to 204H to the circuit board 206, respectively.

Figure 13:
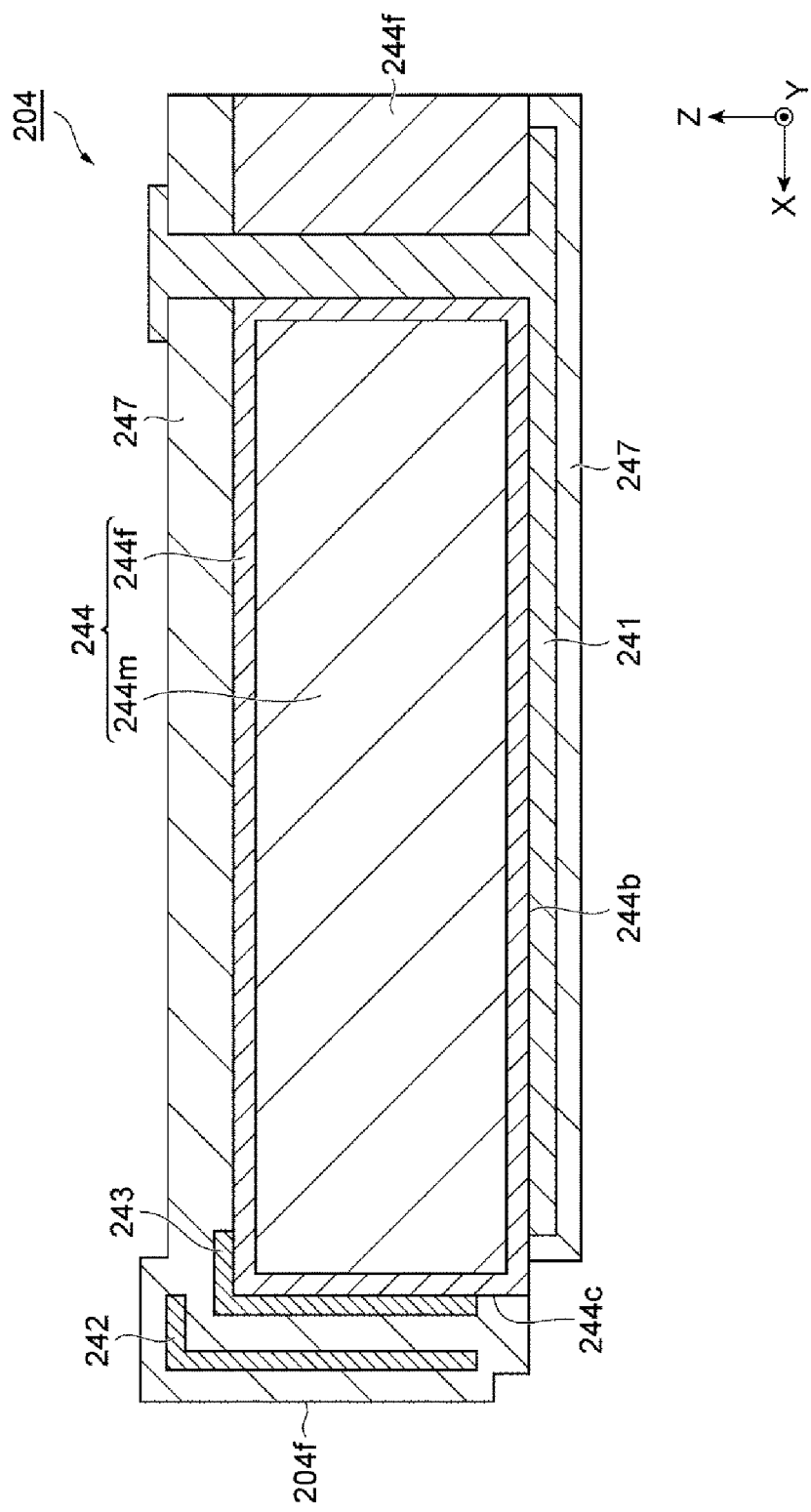
FIG. 13 is a cross sectional view illustrating a sensor chip according to another exemplary embodiment.

Now, a sensor chip according to another exemplary embodiment that can be used as the sensor chips 204A to 204H of the measuring device 200 will be discussed. FIG. 13 is a cross sectional view illustrating the sensor chip according to another exemplary embodiment. The sensor chip 204 shown in FIG. 13 includes a first sensor electrode 241, a second sensor electrode 242, a guard electrode 243 and a substrate member 244.

The substrate member 244 includes a main body 244*m* and an insulating region 244*f*. The main body 244*m* is in an electrically floating state, and may be made of a conductive material or an insulating material. For example, the main body 244*m* is made of silicon. The insulating region 244*f* covers a surface of the main body 244*m*. The insulating region 244*f* may be, by way of example, but not limitation, a thermal oxide film of silicon.

The first sensor electrode 241 faces downward (negative Z direction). According to the present exemplary embodiment, the first sensor electrode 241 is extended along a bottom face of the substrate member 244. The second sensor electrode 242 is formed to face an outside of the edge of the base substrate 202, i.e., to face toward a radial direction with respect to the central axis AX200. In the present exemplary embodiment, the second sensor electrode 242 is extended at the front side from a front end face 244*c* of the substrate member 244. Further, the front end face 244*c* is extended in a direction which intersects with a bottom face 244*b*.

The guard electrode 243 is provided between the first electrode 241 and the second electrode 242. In the exemplary embodiment, the guard electrode 243 is provided between the second sensor electrode 242 and the substrate member 244, and is extended along the front end face 244*c* of the substrate member 244.

According to the exemplary embodiment, the sensor chip 204 further includes an insulating region 247. The insulating region 247 is formed of $SiO_2$, SiN, $Al_2O_3$ or polyimide. The insulating region 247 covers a surface of the substrate member 244, a surface of the first sensor electrode 241, a surface of the second sensor electrode 242 and a surface of the guard electrode 243, and is provided between the second sensor electrode 242 and the guard electrode 243.

Figure 14:
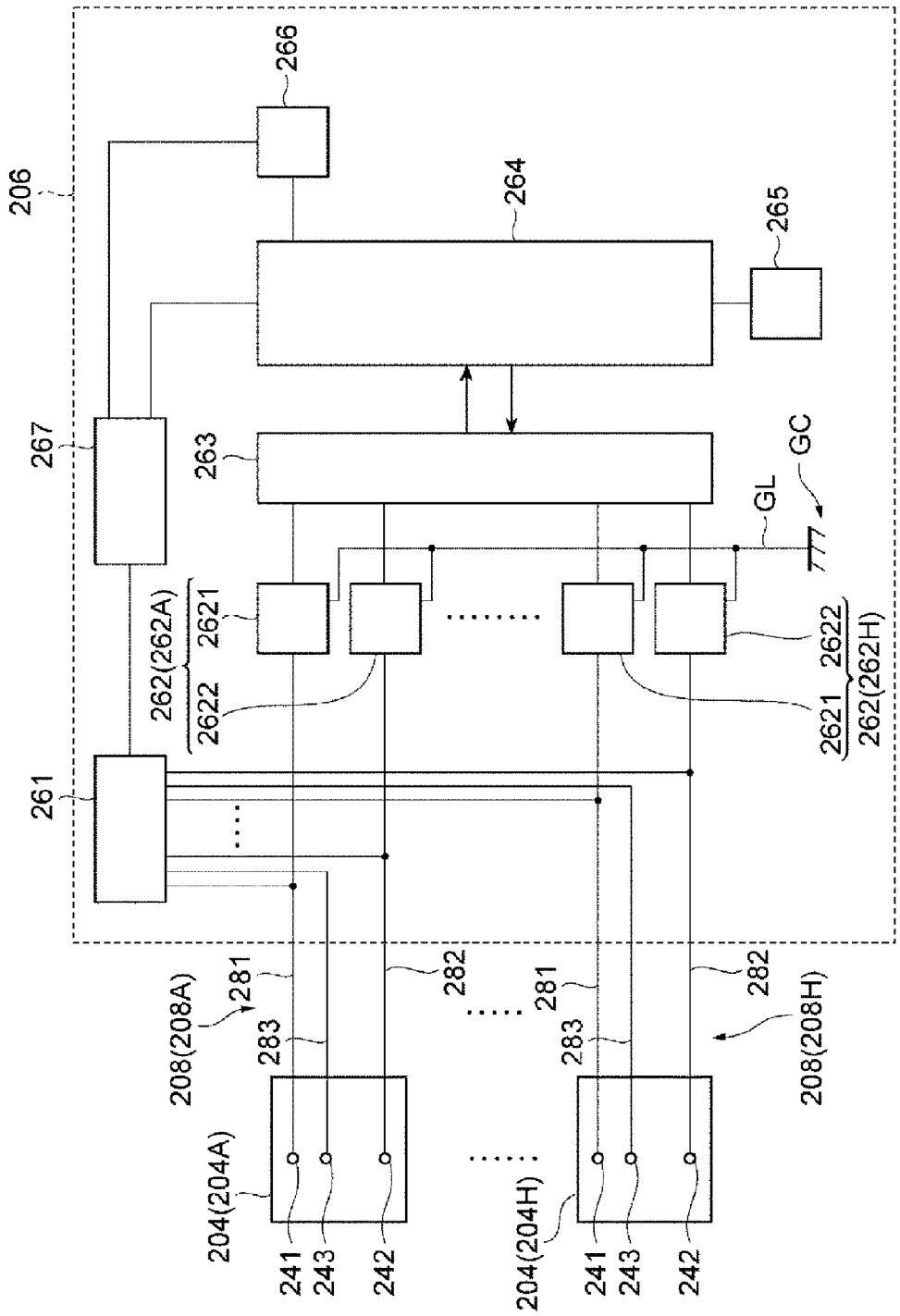
FIG. 14 is a diagram illustrating a configuration of a circuit board according to another exemplary embodiment.

FIG. 14 is a diagram illustrating a configuration of a circuit board according to another exemplary embodiment. The circuit board 206 shown in FIG. 14 includes a high frequency oscillator 261, a plurality of conversion circuit pairs 262A to 262H and an A/D converter 263. Each of the conversion circuit pairs 262A to 262H includes a C/V conversion circuit 2621 and a C/V conversion circuit 2622. In the exemplary embodiment, the circuit board 206 may further include a storage device 265 and a communication device 266. Additionally, in another exemplary embodiment, the circuit board 106 may further include a processor 264 and a power supply 267.

Each of the sensor chips 204A to 204H is connected to the circuit board 206 via each corresponding one of the wiring units 208A to 208H. Further, each of the sensor chips 204A to 204H is connected to each corresponding one of the conversion circuit pairs 262A to 262H via some wirings belonging to each corresponding one of the wiring units. Hereinafter, a single sensor chip 204 having the same configuration as each of the sensor chips 204A to 204H, a single wiring unit 208 having the same configuration as each of the wiring units 208A to 208H and a single conversion circuit pair 262 having the same configuration as each of the conversion circuit pairs 262A to 262H will be explained.

The wiring unit 208 includes wirings 281 to 283. The wiring 281 is configured to connect the first electrode 241 and the C/V conversion circuit 2621 of the conversion circuit pair 262. The wiring 282 is configured to connect the second electrode 242 and the C/V conversion circuit 2622 of the conversion circuit pair 262. The wiring 283 is connected to the guard electrode 243.

The high frequency oscillator 261 is connected to the power supply 267 such as a battery, and is configured to generate a high frequency signal by receiving a power from the power supply 267. Further, the power supply 267 is also connected to the processor 264 and the communication device 266. The high frequency oscillator 261 is equipped with a multiple number of output lines and is configured to output the high frequency signal to the wirings 281 to 283 via the output lines. Accordingly, the high frequency signal from the high frequency oscillator 261 is output to the first sensor electrode 241, the second sensor electrode 242 and the guard electrode 243.

The wiring 281 is connected to an input terminal of the C/V conversion circuit 2621. That is, the first sensor electrode 241 of the sensor chip 204 is connected to the input terminal of the C/V conversion circuit 2621. The C/V conversion circuit 2621 is configured to generate, based on a voltage amplitude at the input terminal thereof, a voltage signal indicating the electrostatic capacitance formed by the first sensor electrode 241 connected to the input terminal thereof, and configured to output the generated voltage signal. Further, as the electrostatic capacitance formed by the first sensor electrode 241 connected to the C/V conversion circuit 2621 increases, the magnitude of the voltage of the voltage signal output from the C/V conversion circuit 2621 also increases.

The wiring 282 is connected to an input terminal of the C/V conversion circuit 2622. That is, the second sensor electrode 242 of the sensor chip 204 is connected to the input terminal of the C/V conversion circuit 2622. The C/V conversion circuit 2622 is configured to generate, based on a voltage amplitude at the input terminal thereof, a voltage signal indicating the electrostatic capacitance formed by the second sensor electrode 242 connected to the input terminal thereof, and configured to output the generated voltage signal. Further, as the electrostatic capacitance formed by the second sensor electrode 242 connected to the C/V conversion circuit 2622 increases, the magnitude of the voltage of the voltage signal output from the C/V conversion circuit 2622 also increases.

Output terminals of the C/V conversion circuits 2621 and 2622 in each of the conversion circuit pairs 262A to 262H are connected to the input terminal of the A/D converter 263. Further, the A/D converter 263 is connected to the processor 264. The A/D converter 263 is controlled by a control signal from the processor 264, and is configured to convert the output signal (voltage signal) from the C/V conversion circuit 2621 in each of the conversion circuit pairs 262A to 262H to a first digital value. Further, the A/D converter 263 is configured to convert the output signal (voltage signal) from the C/V conversion circuit 2622 in each of the conversion circuit pairs 262A to 262H to a second digital value. The A/D converter 263 is also configured to output the first digital value and the second digital value to the processor 264.

The processor 264 is connected to the storage device 265. The storage device 265 is implemented by, by way of non-limiting example, a nonvolatile memory and is configured to store therein the digital values output from the A/D converter 263.

The communication device 266 follows the wireless communication standards. For example, the communication device 266 is based on Bluetooth (registered trademark). The communication device 266 is configured to wirelessly transmit the first digital values and the second digital values stored in the storage device 265.

Now, a method of inspecting the focus ring FR and operations of the individual components of the processing system 1 in performing the method according to another exemplary embodiment will be discussed. FIG. 15 is a flowchart for describing the method of inspecting the focus ring according to another exemplary embodiment. In a method MT2 shown in FIG. 15, the measuring device 200 is used.

A process ST21 of the method MT2 is the same as the process ST1 of the method MT1. In the process ST21, a position of the measuring device 200 is adjusted by the aligner AN. A subsequent process ST22 is the same as the process ST2 of the method MT1. In the process ST22, the measuring device 200 is transferred into a plasma processing apparatus which is employed as one of the process modules PM1 to PM6.

In a subsequent process ST23, the measuring device 200 is scanned by the transfer device TU2. To elaborate, the transfer device TU2 scans the measuring device 200 such that the sensor chips 204A to 204H are moved on the first portion P1 of the focus ring FR and within a region surrounded by the inner periphery P2i of the second portion P2 of the focus ring. While the measuring device 200 is scanned, the measuring device 200 acquires a first digital value indicating electrostatic capacitance based on a voltage amplitude of the first sensor electrode 241 and, also, acquires a second digital value indicating electrostatic capacitance based on a voltage amplitude of the second sensor electrode 242. Then, the measuring device 200 stores first digital values and second digital values obtained while the measuring device 200 is scanned in the storage device 265. Further, the first digital values and the second digital values may be acquired at preset timings under the control of the processor 264.

A subsequent process ST24 is the same as the process ST4 of the method MT1. In the process ST24, the measuring device 200 is taken out from the corresponding process module and returned back into one of the containers 4a to 4d. In a subsequent process ST25, the first digital values and the second digital values stored in the storage device 265 are sent to the operation unit AU. Here, the first digital values and the second digital values may be transmitted from the communication device 266 to the operation unit AU in response to an instruction from the operation unit AU, or may be transmitted to the operation unit AU at preset timing under the control of the processor 264 based on a count of a timer provided at the circuit board 206.

In a subsequent process ST26, the operation unit AU performs a difference operation with respect to the first digital values acquired by the measuring device 200 at multiple positions along the direction which intersects with the inner periphery P2i of the second portion P2 of the focus ring FR. This difference operation is the same operation as the difference operation performed in the process ST6 of the method MT1. Through this operation, the operation unit AU acquires multiple difference values at the multiple positions.

In a subsequent process ST27, the operation unit AU calculates differences between the multiple preset values and the multiple difference values at the multiple positions. Here, the multiple preset values are calculated from multiple digital values obtained at the multiple positions for the focus ring FR in an initial state where the focus ring is not consumed. These preset values may be previously stored in the storage device of the operation unit AU. These differences calculated as stated reflect the consumption amount of the first portion P1 at each position. Further, in the process ST27, the operation unit AU also calculates the consumption amounts of the second portion P2 from the second digital values. By way of example, the operation unit AU may calculate the consumption amounts of the second portion P2 by referring to a table, using the second digital values. Alternatively, the operation unit AU may calculate the consumption amount of the second portion P2 from the second digital values by using a preset function to convert the second digital value to the consumption amount.

The above-stated multiple number of first digital values are obtained based on the voltage amplitude in the first sensor electrode 241 which faces downwards, that is, faces the top face P1t of the first portion P1 of the focus ring FR. Accordingly, the multiple difference values obtained from the first digital values reflect the consumption amounts of the top face P1t of the first portion P1 at the multiple positions. Further, the second digital values are obtained based on the voltage amplitude in the second sensor electrode 242 which faces the outside of the base substrate 202, that is, the inner periphery P2i of the second portion P2 of the focus ring FR. Accordingly, the second digital values reflect the consumption amounts of the inner periphery P2i of the second portion P2. Thus, according to the processing system 1 and the method MT2 using the measuring device 200 equipped with the sensor chip 204, the consumption amounts of the first portion P1 and the second portion P2 can be figured out individually.

Further, according to the sensor chip 204, due to the shield effect by the guard electrode 243, directivity of the first sensor electrode 241 in the downward direction and directivity of the second sensor electrode 242 toward the direction where the second portion P2 of the focus ring is located can be improved.

Further, in the measuring device 200 shown in FIG. 12, the sensor chips 204 (204A to 204H) are mounted to the lower portion 202a of the base substrate 202, as illustrated in FIG. 16. However, the sensor chips 204 (204A to 204H) may be mounted to the upper portion 202b of the base substrate 202, as depicted in FIG. 17.

In the above, the various exemplary embodiments have been described. However, the exemplary embodiments are not limiting and various modifications may be made. For example, the number of the process modules of the processing system 1 may be one or more. Furthermore, in the above description, the capacitively coupled plasma processing apparatus is illustrated as an example of the process module of the processing system 1. However, the plasma processing apparatus that can be used as the process module is not limited thereto, and any type of plasma processing apparatus such as an inductively coupled plasma processing apparatus, a plasma processing apparatus with a surface wave such as a microwave, or the like may be used.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting.

We claim:

1. A system of inspecting a focus ring,
wherein the focus ring is provided on a mounting table configured to mount thereon a processing target object within a processing vessel of a plasma processing apparatus, and the focus ring has an annular plate-shaped first portion and an annular plate-shaped second portion which is extended on the first portion, and a diameter of an inner periphery of the second portion is larger than a diameter of an inner periphery of the first portion, and
the system comprises:
a measuring device, configured to measure electrostatic capacitance, comprising a base substrate having a disk shape; a sensor chip, having a sensor electrode, provided along an edge of the base substrate; and a circuit board configured to output a high frequency signal to the sensor electrode and acquire a digital value indicating electrostatic capacitance based on a voltage amplitude in the sensor electrode;
a transfer device configured to move the sensor chip on the first portion and within a region surrounded by the inner periphery of the second portion by scanning the measuring device; and
an operation unit configured to receive the digital values acquired by the measuring device at multiple positions along a direction which intersects with the inner periphery of the second portion, and configured to obtain difference values at the multiple positions by performing a difference operation with respect to the digital values.

2. The system of claim 1,
wherein the operation unit is configured to calculate a difference between each of the difference values and a preset value corresponding thereto.

3. The system of claim 1,
wherein the circuit board comprises a communication device configured to wirelessly transmit the digital value to the operation unit.

4. A system of inspecting a focus ring,
wherein the focus ring is provided on a mounting table configured to mount thereon a processing target object within a processing vessel of a plasma processing apparatus, and the focus ring has an annular plate-shaped first portion and an annular plate-shaped second portion which is extended on the first portion, and a diameter of an inner periphery of the second portion is larger than a diameter of an inner periphery of the first portion, and
the system comprises:
a measuring device, configured to measure electrostatic capacitance, comprising a base substrate having a disk shape; a sensor chip, provided along an edge of the base substrate, having a first sensor electrode facing downwards and a second sensor electrode facing an outside of the edge of the base substrate; and a circuit board configured to output a high frequency signal to the first sensor electrode and the second sensor electrode and acquire a first digital value indicating electrostatic capacitance based on a voltage amplitude in the first sensor electrode and a second digital value indicating electrostatic capacitance based on a voltage amplitude in the second sensor electrode;
a transfer device configured to move the sensor chip on the first portion and within a region surrounded by the inner periphery of the second portion by scanning the measuring device; and
an operation unit configured to receive the first digital values and the second digital values acquired by the measuring device at multiple positions along a direction which intersects with the inner periphery of the second portion, and configured to obtain difference values at the multiple positions by performing a difference operation with respect to the first digital values.

5. The system of claim 4,
wherein the sensor chip further comprises a guard electrode provided between the first sensor electrode and the second sensor electrode, and the high frequency signal is sent to the guard electrode.

6. The system of claim 4,
wherein the operation unit is configured to calculate a difference between each of the difference values and a preset value corresponding thereto.

7. The system of claim 4,
wherein the circuit board comprises a communication device configured to wirelessly transmit the first digital value and the second digital value to the operation unit.

8. A method of inspecting a focus ring with a measuring device configured to measure electrostatic capacitance,
wherein the focus ring is provided on a mounting table configured to mount thereon a processing target object within a processing vessel of a plasma processing apparatus, and the focus ring has an annular plate-shaped first portion and an annular plate-shaped second portion which is extended on the first portion, and a diameter of an inner periphery of the second portion is larger than a diameter of an inner periphery of the first portion,
the measuring device comprises a base substrate having a disk shape; a sensor chip, having a sensor electrode, provided along an edge of the base substrate; and a circuit board configured to output a high frequency signal to the sensor electrode and acquire a digital value indicating electrostatic capacitance based on a voltage amplitude in the sensor electrode, and
the method comprises:
scanning the measuring device such that the sensor chip is moved on the first portion and within a region surrounded by the inner periphery of the second portion; and obtaining difference values at multiple positions along a direction which intersects with the inner periphery of the second portion by performing a difference operation with respect to the digital values acquired by the measuring device at the multiple positions.

9. The method of claim 8, further comprising:
calculating a difference between each of the difference values and a preset value corresponding thereto.

10. A method of inspecting a focus ring with a measuring device configured to measure electrostatic capacitance,
wherein the focus ring is provided on a mounting table configured to mount thereon a processing target object within a processing vessel of a plasma processing apparatus, and the focus ring has an annular plate-shaped first portion and an annular plate-shaped second portion which is extended on the first portion, and a diameter of an inner periphery of the second portion is larger than a diameter of an inner periphery of the first portion,
the measuring device comprises a base substrate having a disk shape; a sensor chip, provided along an edge of the base substrate, having a first sensor electrode facing downwards and a second sensor electrode facing an outside of the edge of the base substrate; and a circuit board configured to output a high frequency signal to the first sensor electrode and the second sensor electrode and acquire a first digital value indicating electrostatic capacitance based on a voltage amplitude in the first sensor electrode and a second digital value indicating electrostatic capacitance based on a voltage amplitude in the second sensor electrode, and
the method comprises:
scanning the measuring device such that the sensor chip is moved on the first portion and within a region surrounded by the inner periphery of the second portion; and
obtaining difference values at multiple positions along a direction which intersects with the inner periphery of the second portion by performing a difference operation with respect to the first digital values acquired by the measuring device at the multiple positions.

11. The method of claim 10, further comprising:
calculating a difference between each of the difference values and a preset value corresponding thereto.

* * * * *